US010624962B2

(12) United States Patent
Hsu et al.

(10) Patent No.: US 10,624,962 B2
(45) Date of Patent: Apr. 21, 2020

(54) POLYSACCHARIDE CONJUGATION WITH DETOXIFIED E. COLI HEAT LABILE ENTEROTOXIN (LT) USED AS VACCINE

(75) Inventors: Yu-Shen Hsu, Xizhi (TW); I-Ling Kou, Xizhi (TW); Kuo-Chan Hung, Xizhi (TW); Yuan-Hsin Lu, Xizhi (TW); Ta-Tung Yuan, Xizhi (TW)

(73) Assignee: DEVELOPMENT CENTER FOR BIOTECHNOLOGY, Xizhi (TW)

( * ) Notice: Subject to any disclaimer, the term of this patent is extended or adjusted under 35 U.S.C. 154(b) by 104 days.

(21) Appl. No.: 13/097,218

(22) Filed: Apr. 29, 2011

(65) Prior Publication Data

US 2011/0274717 A1 Nov. 10, 2011

Related U.S. Application Data

(60) Provisional application No. 61/330,650, filed on May 3, 2010.

(51) Int. Cl.
*A61K 39/09* (2006.01)
*A61K 39/102* (2006.01)
*A61K 47/64* (2017.01)
*A61K 39/00* (2006.01)

(52) U.S. Cl.
CPC .......... *A61K 39/092* (2013.01); *A61K 39/102* (2013.01); *A61K 47/646* (2017.08); *A61K 47/6415* (2017.08); *A61K 2039/6037* (2013.01)

(58) Field of Classification Search
None
See application file for complete search history.

(56) References Cited

U.S. PATENT DOCUMENTS

| | | | |
|---|---|---|---|
| 2005/0002957 A1* | 1/2005 | Ryall | A61K 39/095 424/190.1 |
| 2007/0065462 A1 | 3/2007 | Ryall | |
| 2007/0207090 A1* | 9/2007 | Giudice | A61K 39/095 424/45 |
| 2008/0095803 A1* | 4/2008 | Mekalanos | 424/237.1 |
| 2008/0102078 A1* | 5/2008 | Hsu et al. | 424/189.1 |
| 2008/0220519 A1 | 9/2008 | Hsu et al. | |
| 2009/0181054 A1 | 7/2009 | Ryall | |
| 2011/0070259 A1* | 3/2011 | Ryall | 424/197.11 |

FOREIGN PATENT DOCUMENTS

| | | |
|---|---|---|
| EP | 0 172 107 A1 | 2/1986 |
| JP | 59-20226 A | 2/1984 |
| JP | 61-502957 A | 12/1986 |
| JP | 2002-533068 A | 10/2002 |
| JP | 2010-533489 A | 10/2010 |
| TW | 095139707 | 5/2008 |
| TW | 200819536 A | 5/2008 |
| WO | 00/37609 A2 | 6/2000 |
| WO | 03/059385 A2 | 7/2003 |
| WO | 2005/103230 A2 | 3/2005 |
| WO | 2009/011707 A1 | 1/2009 |
| WO | 2010/005598 A1 | 1/2010 |

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Bowie et al (Science, 1990, 257:1306-1310).*
Burgess et al (J. of Cell Bio. 111:2129-2138, 1990).*
Sun et al. (PNAS vol. 116 No. 1, pp. 193-198).*
Jakobsen, H., et al., "Intranasal Immunization with Pneumococcal Polysaccharide Conjugate Vaccines Protects Mice against Invasive Pneumococcal Infections", Infection and Immunity, Aug. 1999, vol. 67, No. 8, pp. 4128-4133.
Zhang, P., et al., "Relationship between Polysaccharide Chain Length and Immunogenicity of Pneumococcus Polysaccharide—Protein Conjugate Vaccine Types 1 and 14", Chin. J. Biologicals, Oct. 2007, vol. 20, No. 10, pp. 736-740.
Qiao, R, et al., "Influence of Length of Polysaccharide Fragment on Immunogenicity of *Strepto-coccus pneumoniae* Type 18C Polysaccharide-TT Conjugate", , Chin. J. Biologicals, May 2007, vol. 20, No. 5, pp. 352-355.
Foreign Medical Sciences, Section of Immunology, Jan. 2004, vol. 27, No. 1, pp. 55-58.
Zhu, J., et al., "Construction of Two Gene Plant Expression Vector *E. coli* Heat-labile Enterotoxin A Subunit and B Subunit", Acta Agriculture Boreali-occidentalis Sinica, 2006, 15(5), pp. 140-144 and 162.
Progress in Veterinary Medicine, 2007, 28(2), pp. 85-88.

(Continued)

*Primary Examiner* — Robert A Zeman
(74) *Attorney, Agent, or Firm* — Ladas & Parry LLP

(57) ABSTRACT

A detoxified recombinant *E. coli* heat-labile enterotoxin mutant, LTS61K, is employed as a carrier protein to conjugate polysaccharide. The LTS61K contains a mutated mature sub-unit A (LTA) that includes lysine at amino acid position 61 and a wild-type mature sub-unit B (LTB). Various types of bacterial capsular polysaccharide antigens were chemically conjugated with the LTS61K protein by a reductive amination reaction. The conjugated polysaccharide-LTS61K products were physically, chemically and biochemically identified as soluble form. Rabbits were immunized intramuscularly to determine the immunogenicity of conjugated vaccines by ELISA to detect anti-polysaccharide antigen IgG titers and serum bactericidal assay thereby determining the functional activity of the antibodies. Study results show that conjugated polysaccharide-LTS61K vaccines induce higher polysaccharide-specific IgG titers and greater bactericidal activity in sera than that of polysaccharide alone or polysaccharide mixed with LTS61K. The presence of anti-LTS61K serum IgG antibody alleviates travel diarrhea caused by *E. coli* (ETEC enterotoxigenic *E. coli*).

7 Claims, 23 Drawing Sheets

Specification includes a Sequence Listing.

(56) References Cited

OTHER PUBLICATIONS

European Search Report dated Sep. 6, 2013 for Application No. EP 11817824.3-1403.

Szu, Shousun C., et al., "Laboratory and Preliminary Clinical Characterization of Vi Capsular Polysaccharide-Protein Conjugate Vaccines", Infection and Immunity, Oct. 1994, vol. 62, No. 10, pp. 4440-4444.

Jakobsen, Havard, et al., "Intranasal Immunization with Pneumococcal Polysaccharide Conjugate Vaccines with Nontoxic Mutants of Escherichia coli Heat-Labile Enterotoxins as Adjuvants Protects Mice against Invasive Pneumococcal Infections", Infection and Immunity, Nov. 1999, vol. 67, No. 1, pp. 5892-5897.

Seid, Robert C., Jr., et al., "Chemical Evidence for Covalent Linkages of a Semi-systhetic Glycoconjugate Vaccine for Haemophilus influenzae Type B Disease", Glycoconjugate J (1989) vol. 6, pp. 489-497.

Xiao, Li-Jun, et al., "Preparation of MenA PS-EA Conjugate and its Application in Detection of Capsular Polysaccharide Antibody", Chinese Journal of Biologicals, Jul. 7, 2008, vol. 21, No. 7, pp. 611-614.

Office Action (Notice of Reasons for Rejection) dated Jan. 19, 2016 for Japanese Application No. P2013-508580.

Miyazaki, C., Hib vaccine, Nippon Rinsho, 2008, vol. 66, pp. 1985-1989 with partial English translation.

Da Hora, V. P., et al., "Non-toxic derivatives of LT as potent adjuvants", Vaccine. vol. 29, 2011, pp. 1538-1544.

Liu, L., et al., "Quantitative Proteomic Analysis of Escherichia coli Heat-Labile Toxin B Subunit (LTB) with Enterovirus 71 (EV71) Subunit VP1", International Journal of Molecular Sciences, vol. 17, 2016, pp. 1-20.

\* cited by examiner

Purified PRP-LTS61K conjugates analyzed by IEF PAGE to confirm the purity of purified conjugate vaccine (pH 3-10 IEF PAGE)

1. LT only
2. 1.5:1 conjugate LMW
3. 3:1 conjugate LMW
4. 5:1 conjugate LMW
5. 10:1 conjugate
6. 1.5:1 conjugate HMW
7. 3:1 conjugate HMW
8. 5:1 conjugate HMW

Figure 14

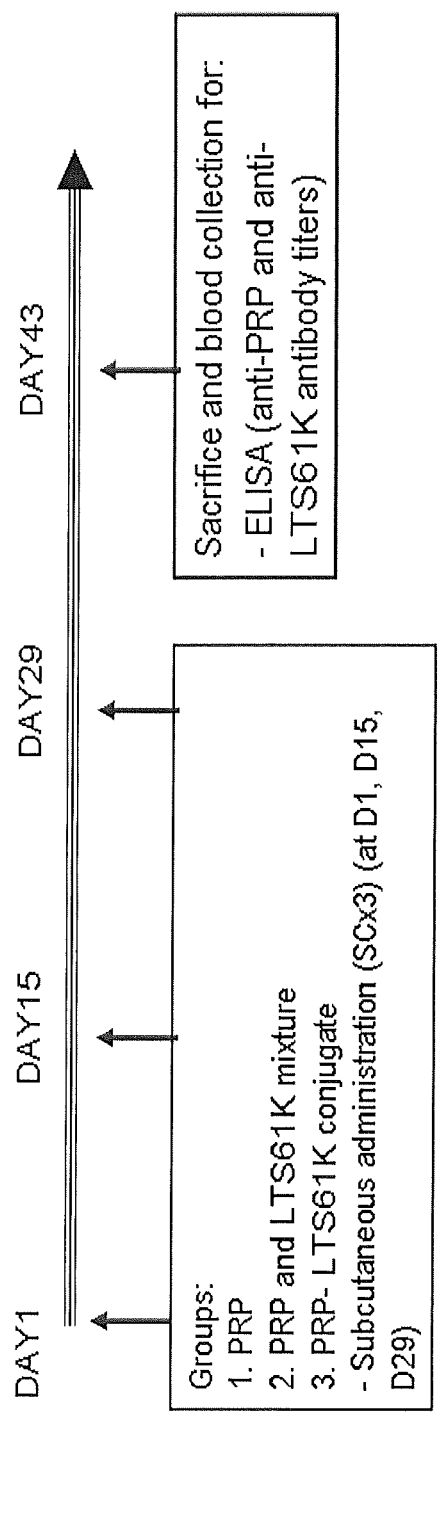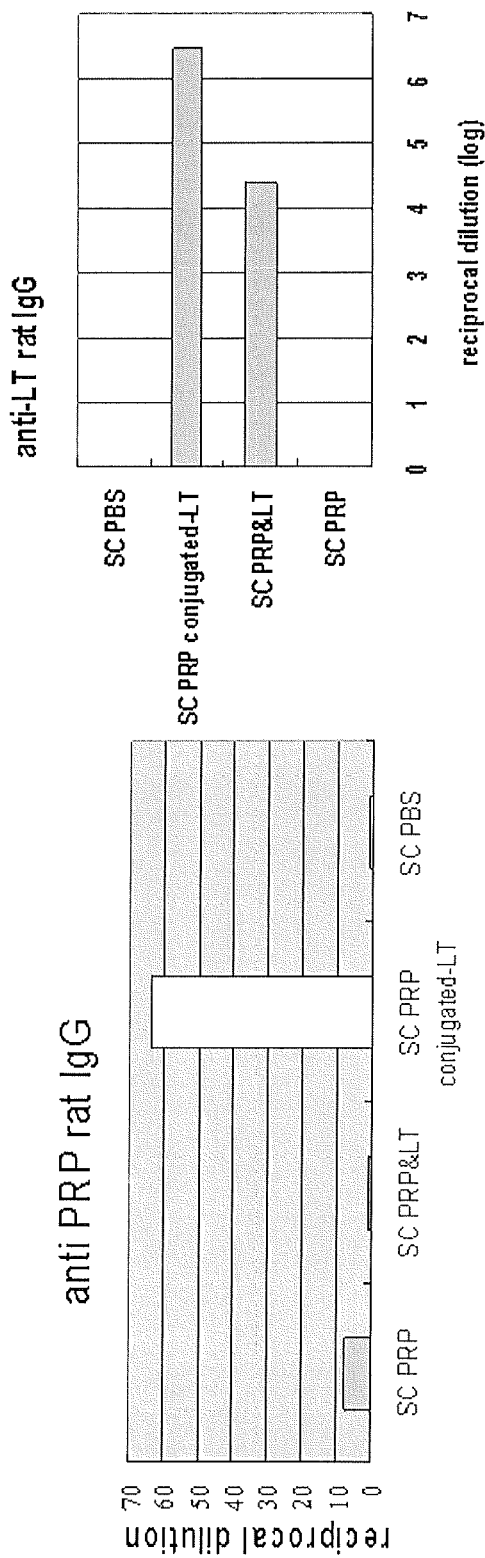
Figure 15

POLYSACCHARIDE CONJUGATION WITH DETOXIFIED E. COLI HEAT LABILE ENTEROTOXIN (LT) USED AS VACCINE

CROSS-REFERENCE TO RELATED APPLICATIONS

Priority is claimed to U.S. Provisional Patent Application Ser. No. 61/330,650, filed on May 3, 2010, the disclosure of which is incorporated herein by reference in its entirety.

SUBMISSION OF SEQUENCE LISTING

The Sequence Listing associated with this application is filed in electronic forma via EFS-Web and hereby incorporated by reference into the specification in its entirety. The name of the text file containing the Sequence Listing is Sequence_Listing_15356_00006. The size of the text filed is 11 KB, and the text file was created on Jul. 18, 2011.

BACKGROUND OF THE INVENTION

Polysaccharide vaccines, when prepared without carrier protein, lack immune memory responses. Currently known conjugated vaccines include bacterial capsular polysaccharides such as *Haemophilus influenzae* type b, *Neisseria meningitidis* group C, and *Streptococcus pnemoniae* serotypes 1, 3, 4, 5, 6B, 7F, 9V, 14, 19F, 23F. These vaccines are covalently conjugated to a carrier protein, such as *tetanus* toxoid, *diphtheria* toxoid, CRM197, a mutant nontoxic *diphtheria* toxin, or *Neisseria meningitidis* outer membrane protein. These polysaccharide conjugate vaccines could induce T-cell dependent response, especially in infants below the age of two years; and they could prime long term immunologic memory, produce high affinity antibody, and could lower the rate of nasopharyngeal colonization and transmission.

However, the majority of the currently marketed bacterial polysaccharide conjugate vaccines applied tetanus toxoid (TT) or diphtheria toxoid (DT) as a carrier protein. TT and DT, these two toxoid proteins, are regular vaccines for infants/children; high frequency vaccination of TT and DT within a short time could have impact on the immunogenicity and safety. (Reduced response to multiple vaccines sharing common protein epitopes that are administered simultaneously to infants. Infect. Immun. 1998; 66(5):2093-8; Immunogenicity and safety of a combination pneumococcal-meningococcal vaccine in infants: a randomized controlled trial. JAMA 2005; 293(14):1751-8). Therefore, this invention provides a new type of the carrier protein LTS61K for its use on the conjugate vaccine.

SUMMARY OF THE INVENTION

This invention includes polysaccharide conjugation with a detoxified *E. coli* heat labile enterotoxin (LT) useful as vaccine to protect or immunize against the effects of infectious bacteria such as *Haemophilus influenzae* and *Streptococcus pneumoniae* and alleviate travel diarrhea caused by enterotoxigenic *E. coli*.

One aspect of this invention relates to covalently conjugated polysaccharide-LTS61K vaccines isolated in purified form. These conjugated products have unexpectedly superior immunogenic and bactericidal properties in mammals. Another aspect relates to a method of administering an effective amount of conjugated polysaccharide-LTS61K vaccine to a mammal in need of protection from *Haemophilus influenzae* type b (Hib). The vaccines of the present invention stimulate T-helper cell response, exhibit strong booster response upon re-exposure and have high antibody titers.

Yet another aspect of the invention relates to the method of producing conjugated polysaccharide-LTS61K by reductive amination and isolating purified conjugated product. In accordance with the present invention, it was discovered that the preferred method of conjugating polysaccharide and LTS61K for making the vaccine of the present invention is periodate oxidation of native PS followed by reductive amination.

The LTS61K employed in the conjugates of the present invention is described in PCT Application Number PCT/US2007/075801, filed Aug. 13, 2007; in U.S. Applications Numbers US11/779,419 filed Jul. 18, 2007, U.S. Ser. No. 12/120,953 filed May 15, 2008, and U.S. Ser. No. 12/729, 649 filed Mar. 23, 2010; and in Taiwan Patent Application No. 95139707 filed Oct. 27, 2006 and issued January 2009. The subject matter described in each of these applications is hereby incorporated by reference.

BRIEF DESCRIPTION OF THE FIGURES

FIG. 14 shows purified PRP-LTS61K conjugates analyzed by IEF PAGE to confirm the purity of purified conjugate vaccine.

FIG. 15 summarizes a rat immunogenicity study of Hib PRP-LTS61K conjugates of the present invention.

DETAILED DESCRIPTION OF THE INVENTION

We have now discovered that conjugated polysaccharide-LTS61K vaccines made in accordance with the present invention surprisingly induce higher polysaccharide-specific IgG antibody titers and greater bactericidal activity in sera than that of polysaccharide or polysaccharide mixed with LTS61K.

Figure 1:
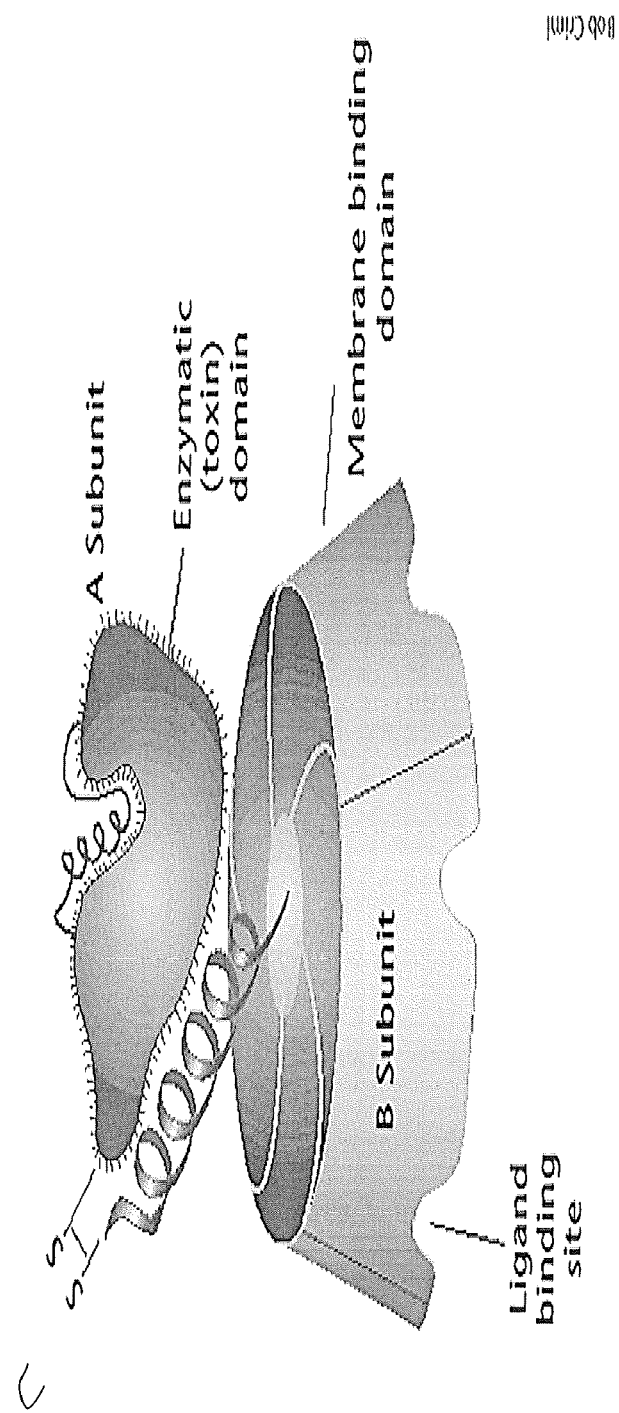
FIG. 1 is a generalized depiction of a LT carrier protein.

A list of abbreviations employed herein is as follows:
CFU: colony forming unit
ELISA: enzyme linked immunosorbent assay
Hib: *Haemophilus influenzae* type b
IEF: isoelectric focusing
LT: heat labile enterotoxin
MALLS: multiple angle laser light scattering
OD: optical density
PNPS: pneumococcal polysaccharide
PRP: polyribosyl ribitol phosphate
PS: polysaccharide
SDS-PAGE: sodium dodecyl sulfate polyacrylamide gel electrophoresis
SEC_HPLC: size exclusion high pressure liquid chromatography
RI: reflective index The new carrier protein employed in the conjugates of the present invention is detoxified recombinant *E. coli* heat-labile enterotoxin mutant, LT, more specifically LTS61K. In the LT mutant, the A and B sub-units form a typical $AB_5$ holotoxin structure. The detoxified LT mutant (LTS61K) contains a mutated mature sub-unit A (LTA) that includes K at amino acid position 61 and a wild-type mature sub-unit B (LTB). LTS61K renders the product significantly less toxic than wild-type LT. The carrier protein is depicted in FIG. 1 of the drawings.

The invention of the LTS61K, which was selected as one of the starting materials for the present invention, is based on the unexpected discovery that an LT containing a mutated LTA exhibits reduced toxicity compared to its wild type counterpart while retaining immunogenicity. This mutated LTA has an amino acid substitution at the position corresponding to position 61 of a wild-type LTA, whose amino acid sequence is shown in SEQ ID NO:1. Accordingly, LTS61K features an isolated polypeptide including a mutated LTA that contains an amino acid residue other than S, T, and F, at the position corresponding to position 61 of SEQ ID NO:1. The substituting amino acid residue can be D, E, H, I, K, L, N, P, Q, R, Y or W. It can be a naturally occurring amino acid or a non-naturally occurring amino acid, e.g., a D-amino acid or a β-amino acid. In one example, the LTA has the amino acid sequence of SEQ ID NO:2, 3, 4 or 5. An LT containing this mutated LTA exhibits reduced toxicity, i.e., <10-5-fold that of a wild-type LT containing SEQ ID NO:1.

Figure 2:
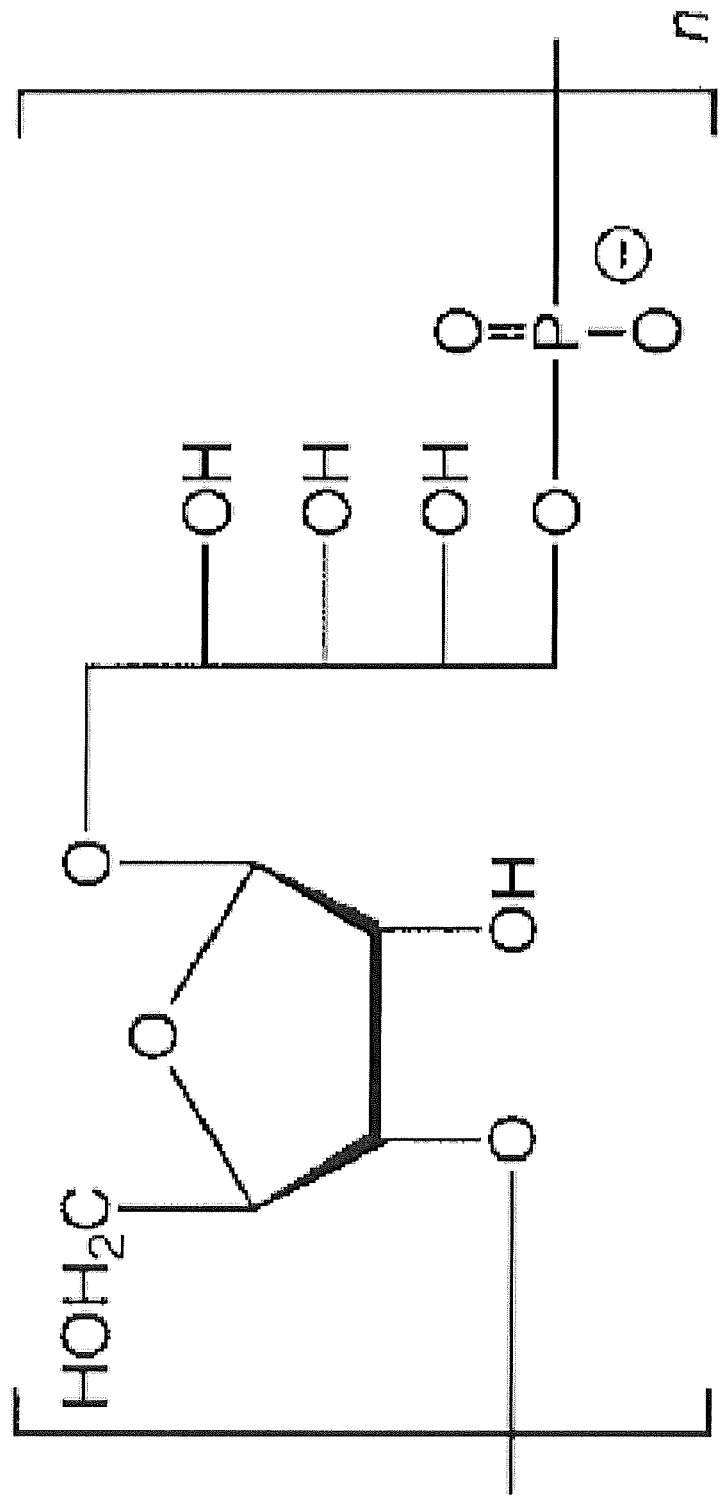
FIG. 2 is the structural representation of Hib PRP saccharides.

In accordance with the present invention, *Haemophilus influenzae* type B was cultured and its capsular polysaccharide antigen, polyribosylribitol phosphate (PRP), was purified. The PRP is linear, has a negative charge and is hydrophilic. The Hib PRP saccharide with molecular weight 345 and formula 10C, 18H, 11O, 1P is depicted as in FIG. 2 of the drawings.

PRP is conjugated onto LTS61K by a chemical reductive amination reaction employing appropriate molar ratios of polysaccharide PRP to protein (LTS61K) which produce conjugate vaccines. Ranges of molar ratios of PRP:LTS61K are shown in Table 1, below. Preferably, the range of molar ratios of PRP:LTS61K is between about 3:1 and about 60:1, and mole/mole $10_4^-$/PRP is between about 0.1 and about 0.4.

TABLE 1

Different ratios of PRP/LTS61K conjugation test

| PRP:LTS61K (w:w) | PRP:LTS61K (m:m) | $IO_4^-$/PRP repeat unit (m/m) | Average repeat unit PRP (Colorimetric assay) | Reaction time | PRP/Protein LTS61K (w/w) | PRP/Protein LTS61K (m/m) |
|---|---|---|---|---|---|---|
| 0.5:1 | 3:1 | 0.1 | 42 | 2 weeks | 0.059 | 0.68 |
| 1:1 | 6:1 | 0.1 | 42 | 2 weeks | 0.099 | 1.14 |
| 1.5:1 | 9:1 | 0.1 | 42 | 2 weeks | 0.13 | 1.5 |
| 2:1 | 28:1 | 0.2 | 17.5 | 2 weeks | 0.21(10/48) | 3 |
| 3:1 | 42:1 | 0.2 | 17.5 | 2 weeks | 0.23 | 3.2 |
| 4:1 | 56:1 | 0.2 | 17.5 | 2 weeks | 0.24 | 3.4 |
| 3:1 | 42:1 | 0.2 | 17.5 | 3 weeks | 0.21 | 2.9 |
| 3:1 | 42:1 | 0.2 | 17.5 | 4 weeks | 0.35 | 4.9 |
| 3:1 | 42:1 | 0.2 | 17.5 | 5 weeks | 0.33 | 4.6 |
| 3:1 | 42:1 | 0.2 | 17.5 | 6 weeks | 0.31 | 4.3 |
| 3:1 | 50:1 | 0.3 | 14.2 | 2 weeks | 0.34 | 5.8 |
| 3:1 | 60:1 | 0.4 | 12.2 | 2 weeks | 0.37(10/27) 0.5(10/20) | 7.4 |

Further in accordance with the present invention, a variety of different types of the bacterial capsular polysaccharides antigens from *Haemophilus influenzae* type b and *Streptococcus pneumoniae* are chemically conjugated with the LTS61K protein by reductive amination reactions. A variety of different molar ratios of $NaIO_4$:PRP as shown in Table 1, above, were employed to oxidize polysaccharides to produce short lengths of polysaccharides with different repeating units. Following the proper molar ratio of the polysaccharide reacted with LTS61K, the successfully conjugated and purified polysaccharide-LTS61K conjugate products were obtained. The products were in soluble form and were physically and chemically evaluated by SEC-HPLC, orcinol, SDS-PAGE, western blotting, IEF, GM1-binding activity, circular dichroism and fluorescent assays to identify the successful chemical conjugation of the polysaccharide antigen and LTS61K carrier protein.

Figure 3:
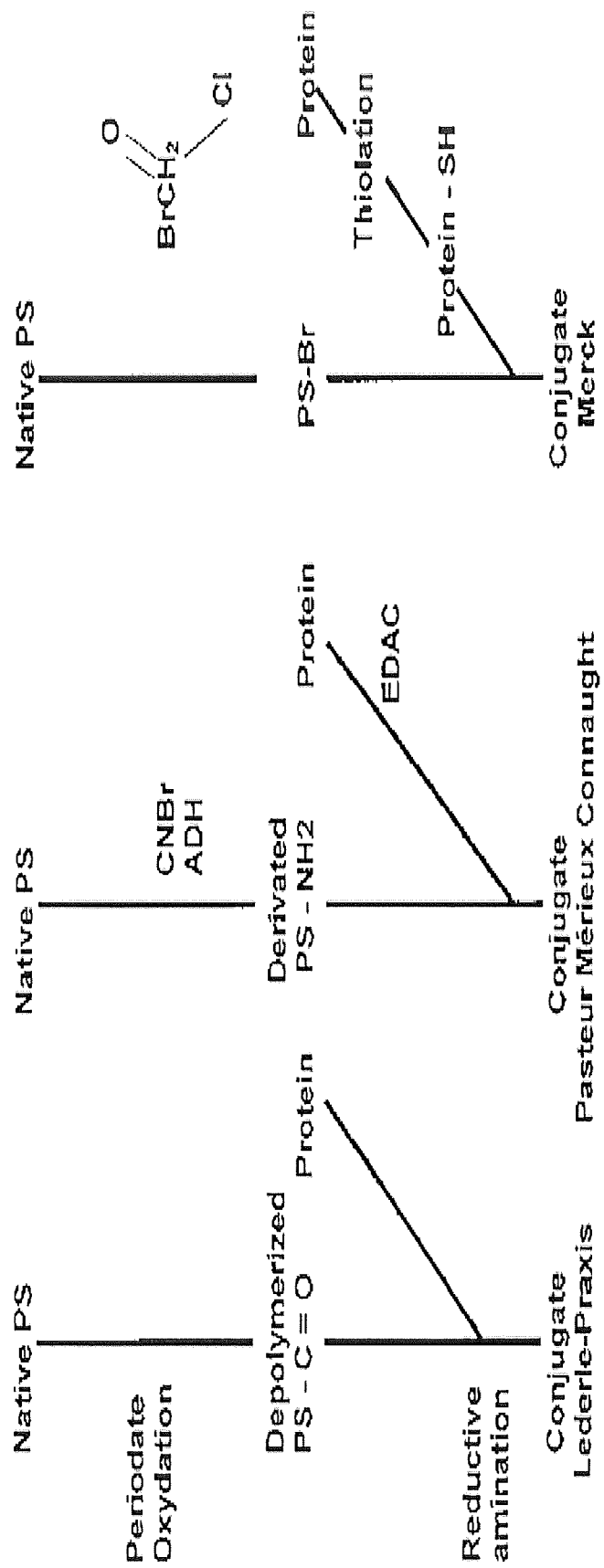
FIG. 3 shows several conjugation methods.
Figure 4:
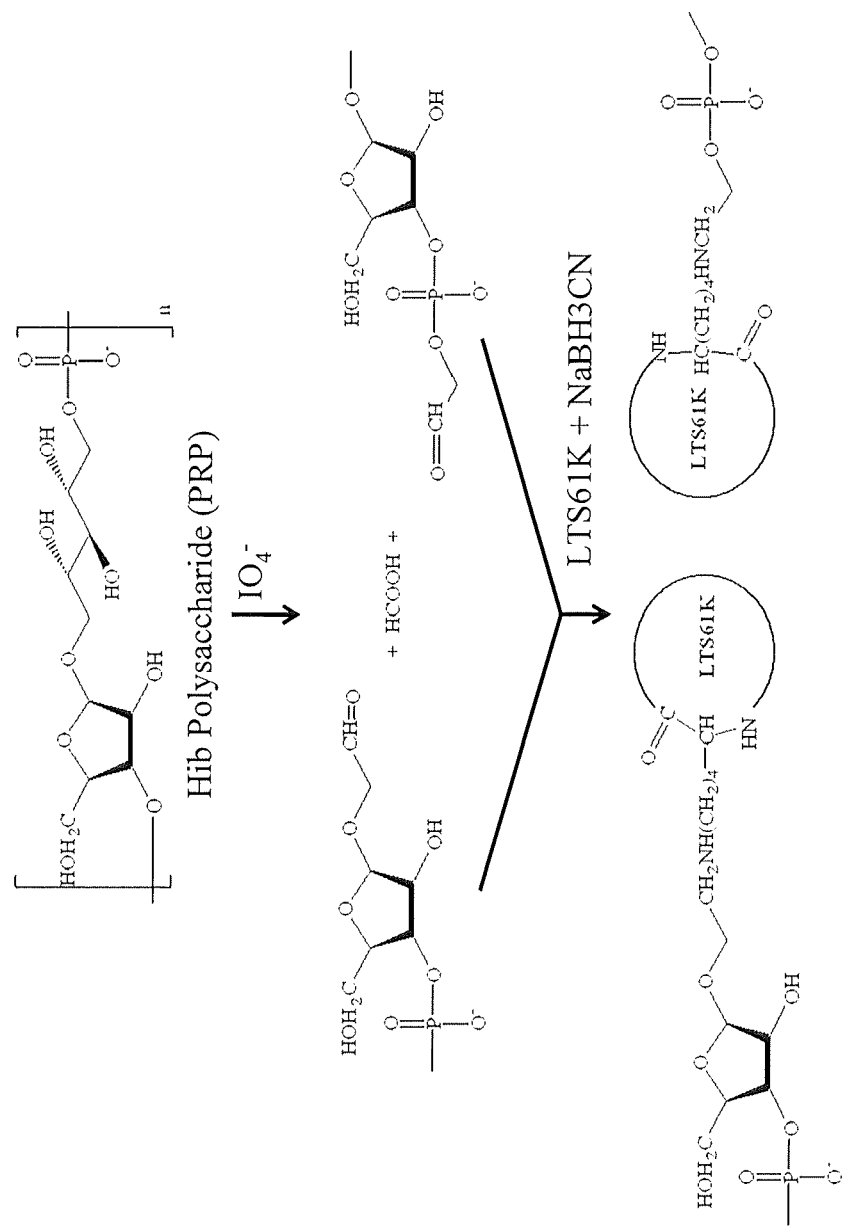
FIG. 4 shows a reductive amination method according to the present invention.

Example of the Procedure of Making Polysaccharide Conjugated with LTS61K:

A variety of potential conjugation processes are illustrated in FIG. 3 of the drawings. A generalized flow diagram of the reductive amination process selected in accordance with the present invention is found at Glycoconjugate J. 1989.6:489 and is reproduced as FIG. 4 of the drawings.

In accordance with the present invention, a polysaccharide is cleaved by periodate oxidation to smaller fragments to produce aldehyde end groups. Thereafter, conjugation of the oxidized polysaccharide to LTS61K protein is carried out by reductive amination. More specifically, an example of the process is as follows:

A. Polysaccharide activation (periodate oxidation): Native polyribosylribitol phosphate (PRP), which is purified capsular polysaccharide of *Haemophilus influenzae* type b, in an amount of 5 mg/mL is mixed with periodate $IO_4^-$) 0.3 or 0.6 or 1.2 mg/mL (molar ratio (m/m) of $IO_4^-$ to PRP=0.1, 0.2, 0.4). This mixture was allowed to stand at 4° C. in the dark for 24 hours. Then glycerol was added to terminate the reaction. The resulting oxidized PRP underwent dialysis against $ddH_2O$ using 3.5 K membrane to remove impurities. The resulting product was sterile filtered with 0.22 um filter. The periodate oxidation procedure provided fragmentation of the polysaccharide PRP into different chain lengths. The range of average number of repeating units of PRP was about 40 to 10.

B. Polysaccharide-LTS61K conjugation: Preparation of PRP and LTS61K conjugate, mixture of oxidized PRP obtained from above, purified LTS61K (which was disclosed in the previous obtained/filed patents) and sodium cyanoborohydride ($NaBH_3CN$), in 10 mg/mL, 3 mg/mL and 10 mg/mL, respectively, the reaction was carried for 2 weeks at 4° C. in the dark. The reaction was terminated by adding sodium borohydride $NaBH_4$ to quench unreacted aldehydes on PRP, the preparation was then dialyzed against $ddH_2O$ with 10 K membrane.

Figure 5:
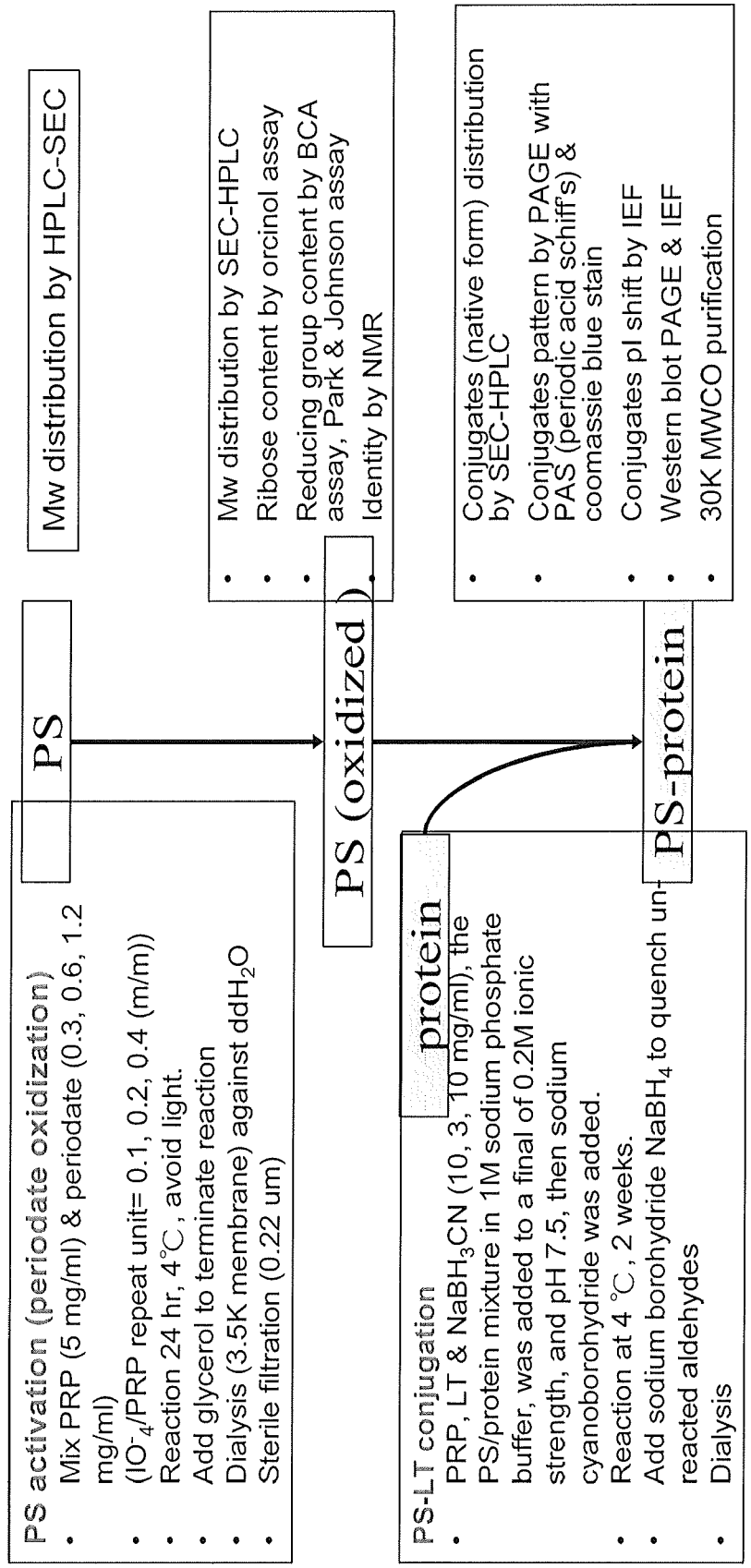
FIG. 5 depicts PRP and LTS61K conjugation by reductive amination.

C. Characterization of the polysaccharide conjugated LTS61K products: Following the proper molar ratio of the polysaccharide reacted with LTS61K, the successfully conjugated and purified polysaccharide-LTS61K conjugate products were obtained. The products with soluble form were physically, chemically and biologically evaluated by SEC-HPLC, Orcinol, SDS-PAGE, Western blotting, IEF, GM1-binding activity, circular dichroism and fluorescent assays to confirm the successful chemical conjugation of the polysaccharide antigen and LTS61K carrier protein, ratio of polysaccharide to LTS61K protein, and its immunogenicity. FIG. 5 of the drawings summarizes reaction conditions and assays employed in accordance with specific exemplification of the present invention.

Reference is now made to the Figures of drawings which pertain to confirmation of structure and purity of the conjugates and vaccine.

Figure 6:
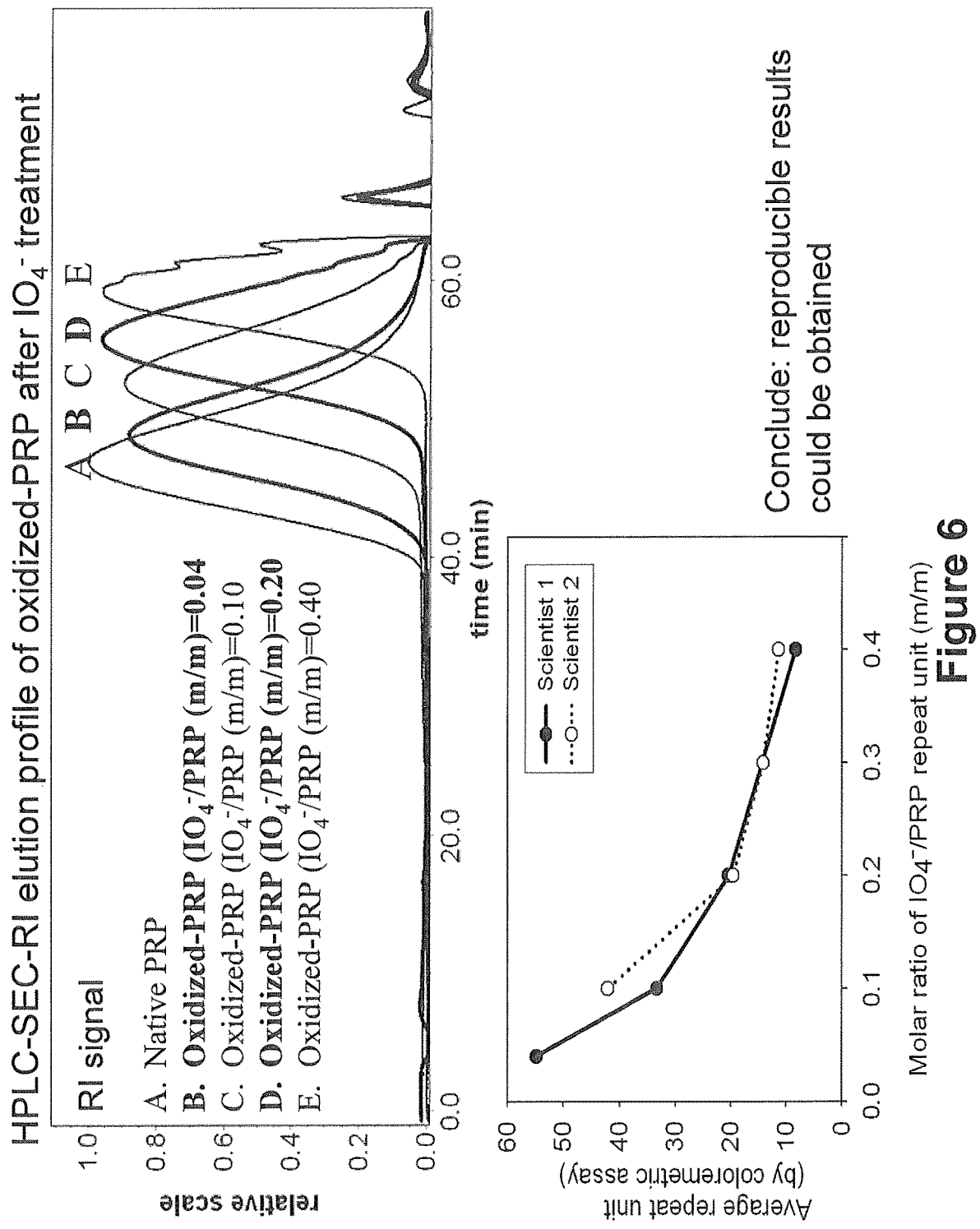
FIG. 6 shows the HPLC-SEC-RI elution profile of oxidized-PRP after $NaIO_4$ treatment.

FIG. 6 shows the HPLC-SEC-RI elution profile of oxidized-PRP after $NaIO_4$ treatment, This figure illustrates the process of the invention and results are readily reproducible.

Figure 7:
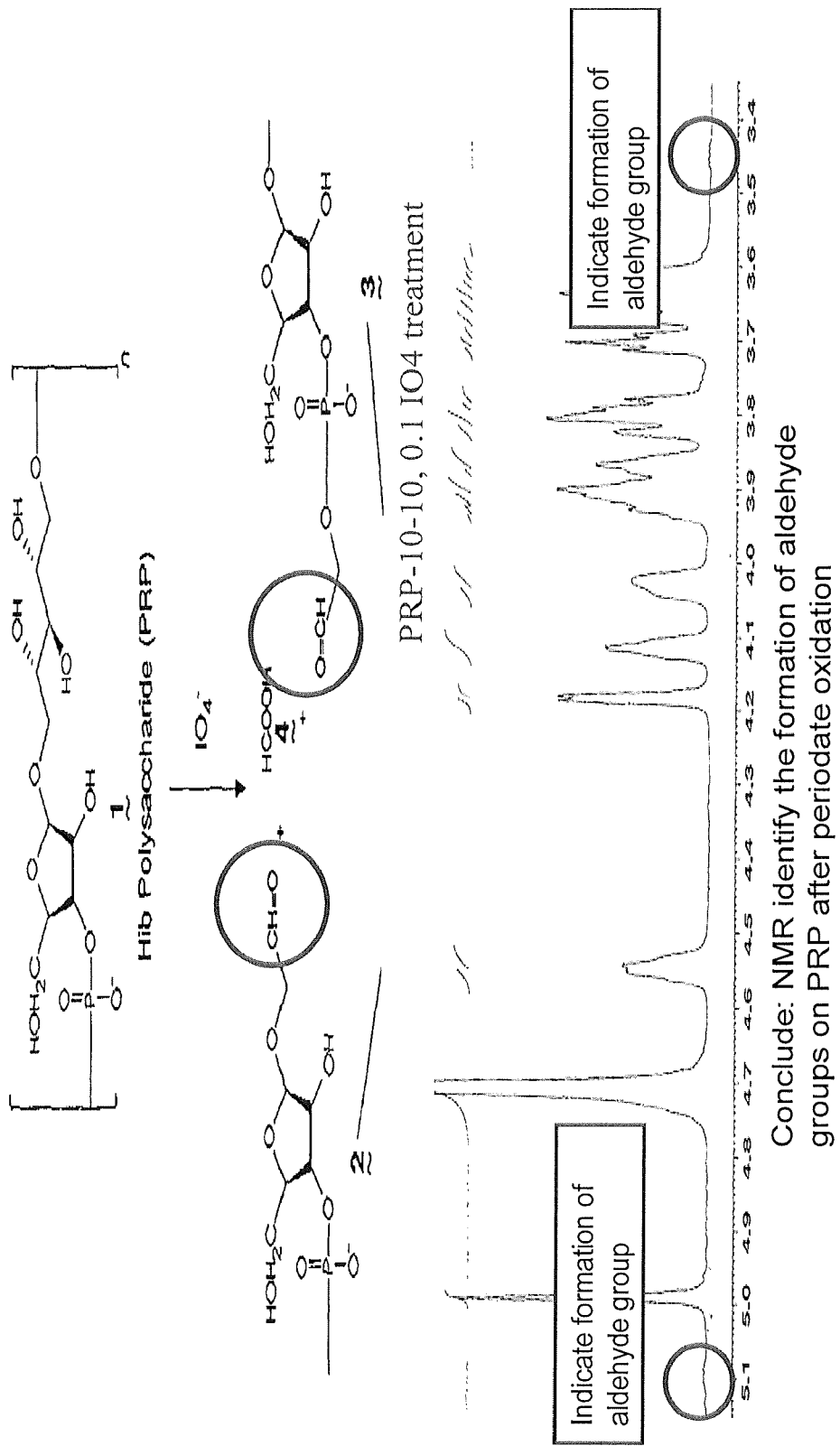
FIG. 7 is an NMR spectrum of oxidized-PRP. This confirms the formation of aldehyde groups on PRP after periodate oxidation.

FIG. 7 is an NMR spectrum of oxidized-PRP. This confirms the formation of aldehyde groups on PRP after periodate oxidation.

Figure 8:
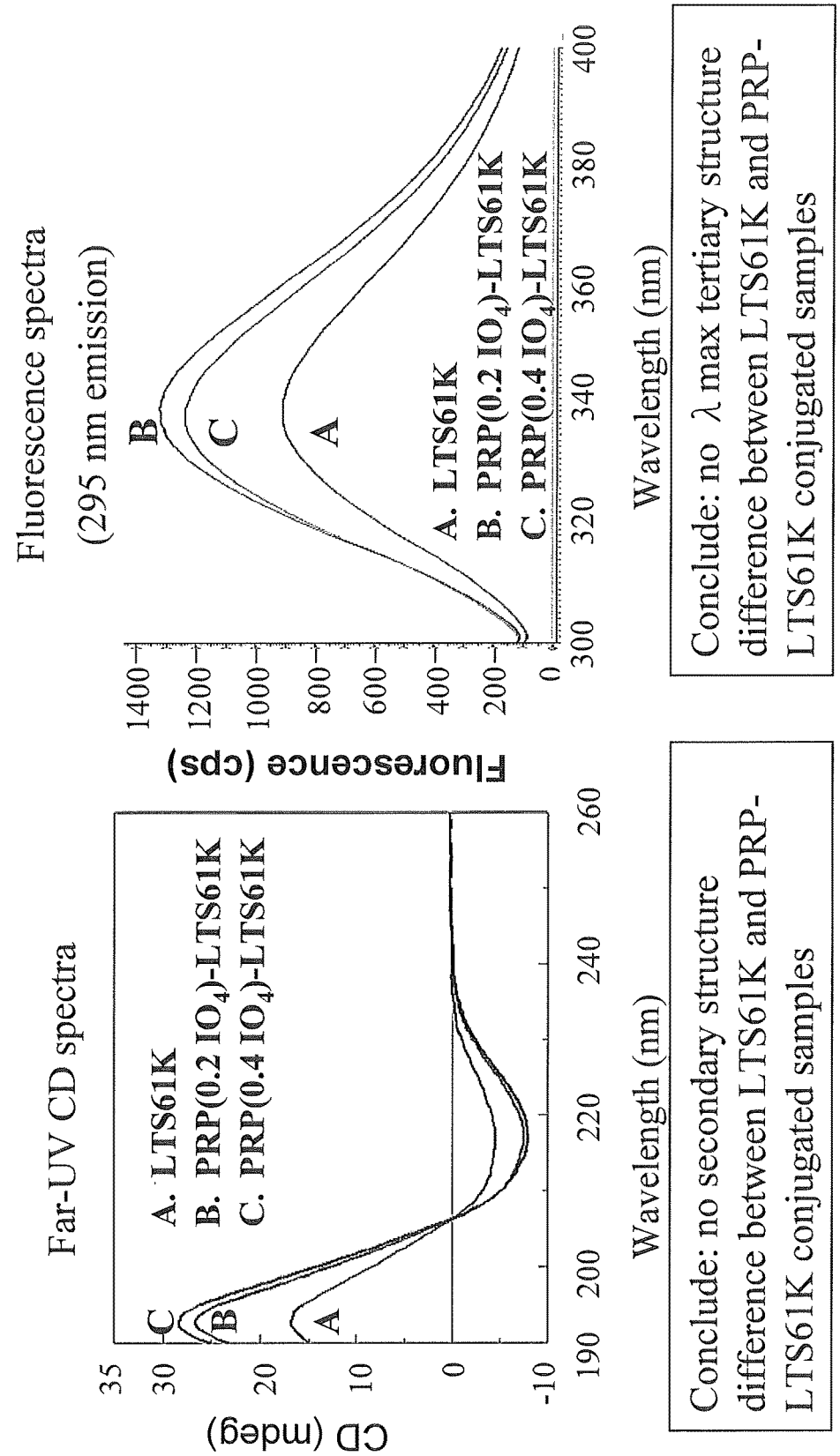
FIG. 8 shows a Far-UV CD spectra that confirms no secondary structure difference between LTS61K and PRP-LTS61K conjugated samples; and also a Fluorescence spectra which confirms no λ max tertiary structure difference between LTS61K and PRP-LTS61K conjugated samples.

FIG. 8 shows a Far-UV CD spectra that confirms no secondary structure difference between LTS61K and PRP-LTS61K conjugated samples; and also a fluorescence spectra which confirms no λ max tertiary structure difference between LTS61K and PRP-LTS61K conjugated samples.

Figure 9:
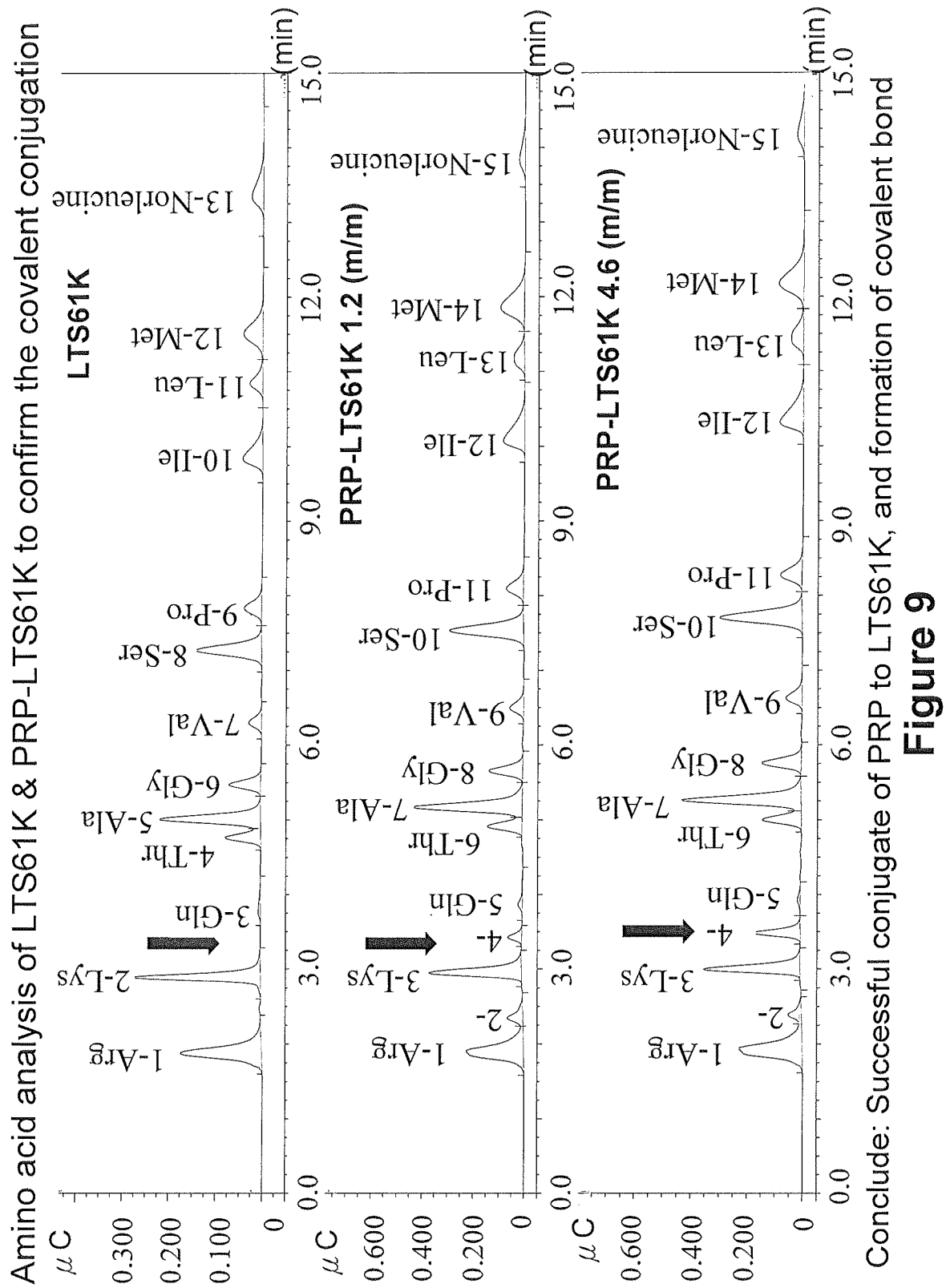
FIG. 9 shows amino acid analyses that confirm the successful conjugation of PRP to LTS61K and the formation of a covalent bond.

FIG. 9 shows amino acid analyses that confirm the successful conjugation of PRP to LTS61K and the formation of a covalent bond.

Figure 10:
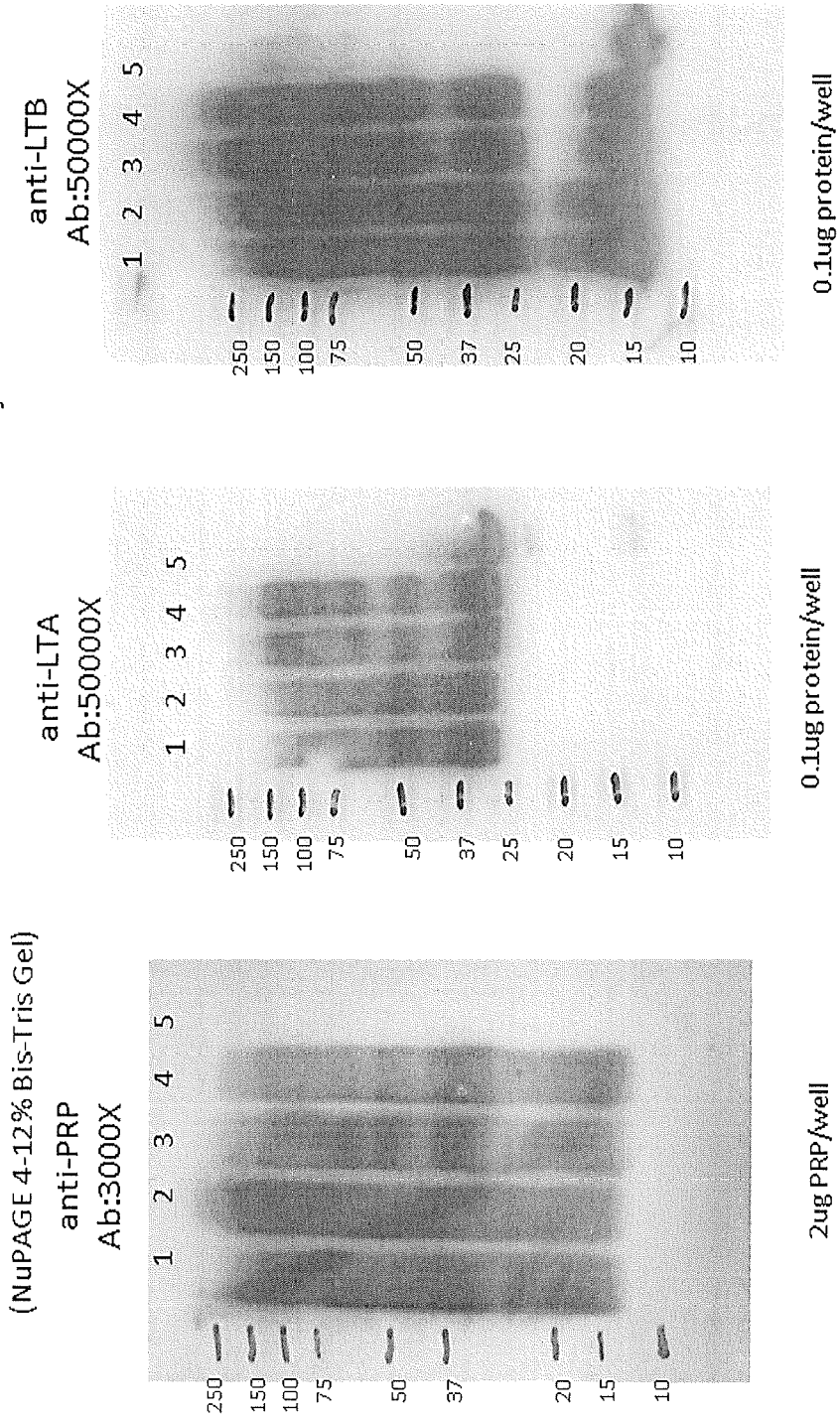
FIG. 10 shows SDS-PAGE Western Blotting analysis to confirm the covalent conjugation between PRP and LTS61K.

FIG. 10 shows SDS PAGE Western Blotting analysis to confirm the covalent conjugation between PRP and LTS61K.

Figure 11:
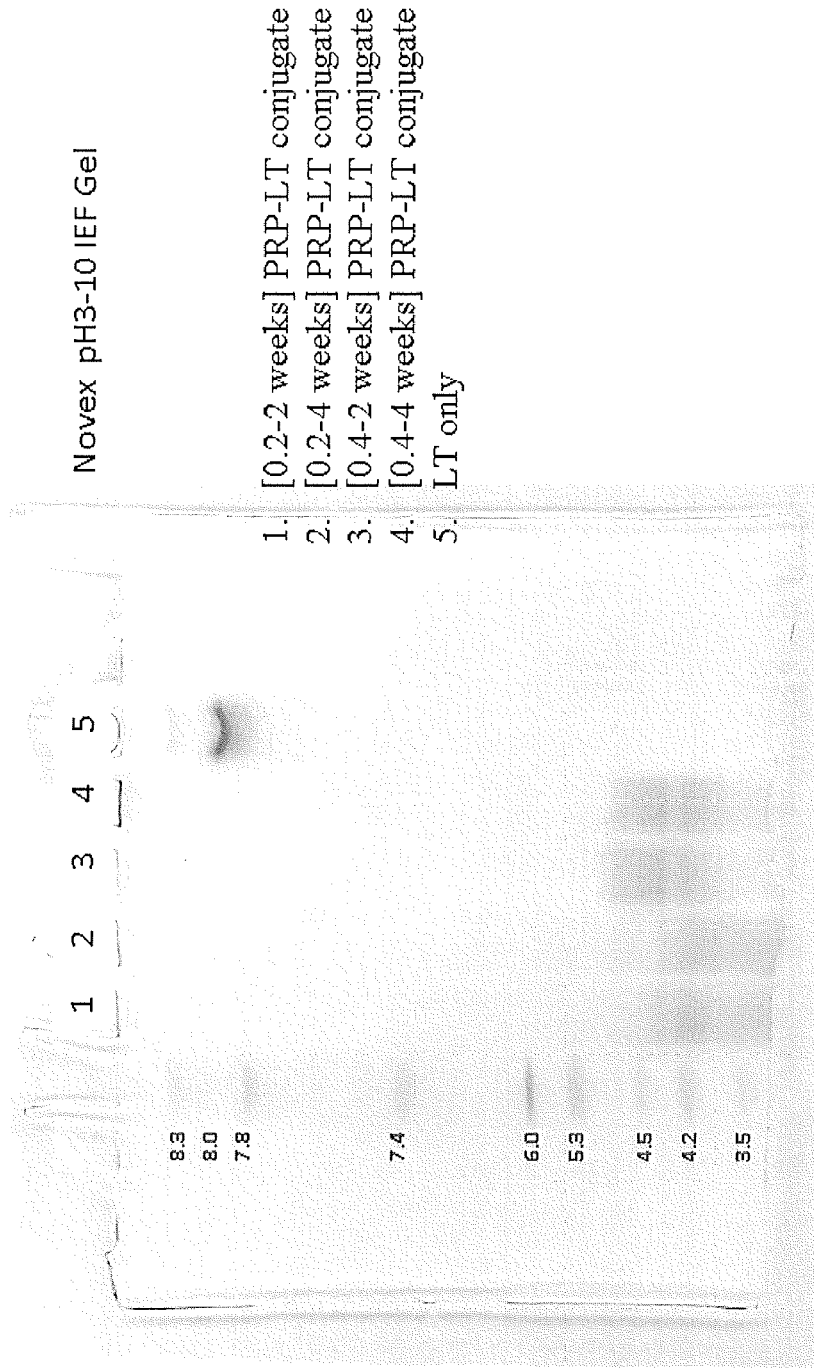
FIG. 11 shows purified PRP-LTS61K conjugates analyzed by IEF PAGE.

FIG. 11 shows purified PRP-LTS61K conjugates analyzed by IEF PAGE.

Figure 12:
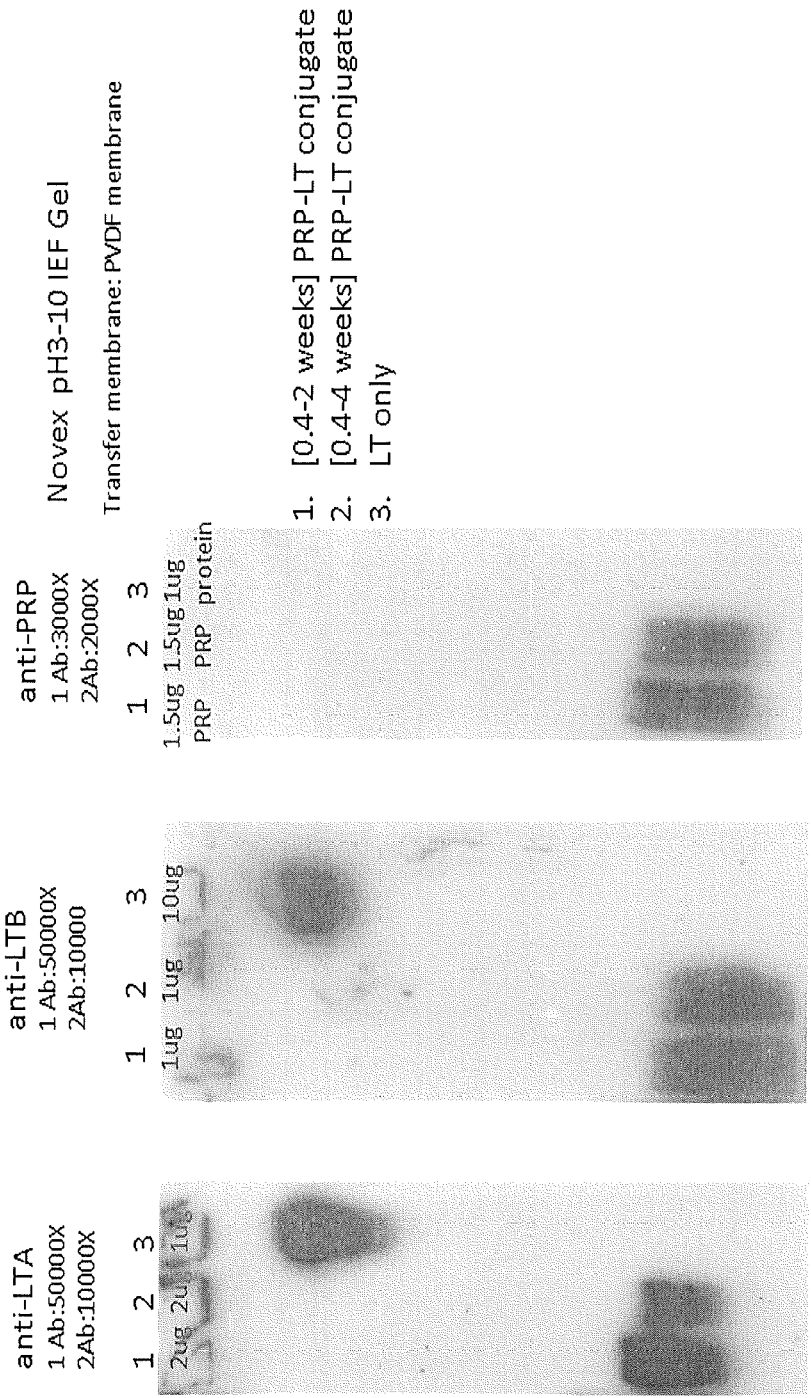
FIG. 12 shows IEF Western Blotting to confirm the covalent conjugation between PRP and LTS61K.

FIG. 12 shows IEF Western Blotting to confirm the covalent conjugation between PRP and LTS61K.

Figure 13:
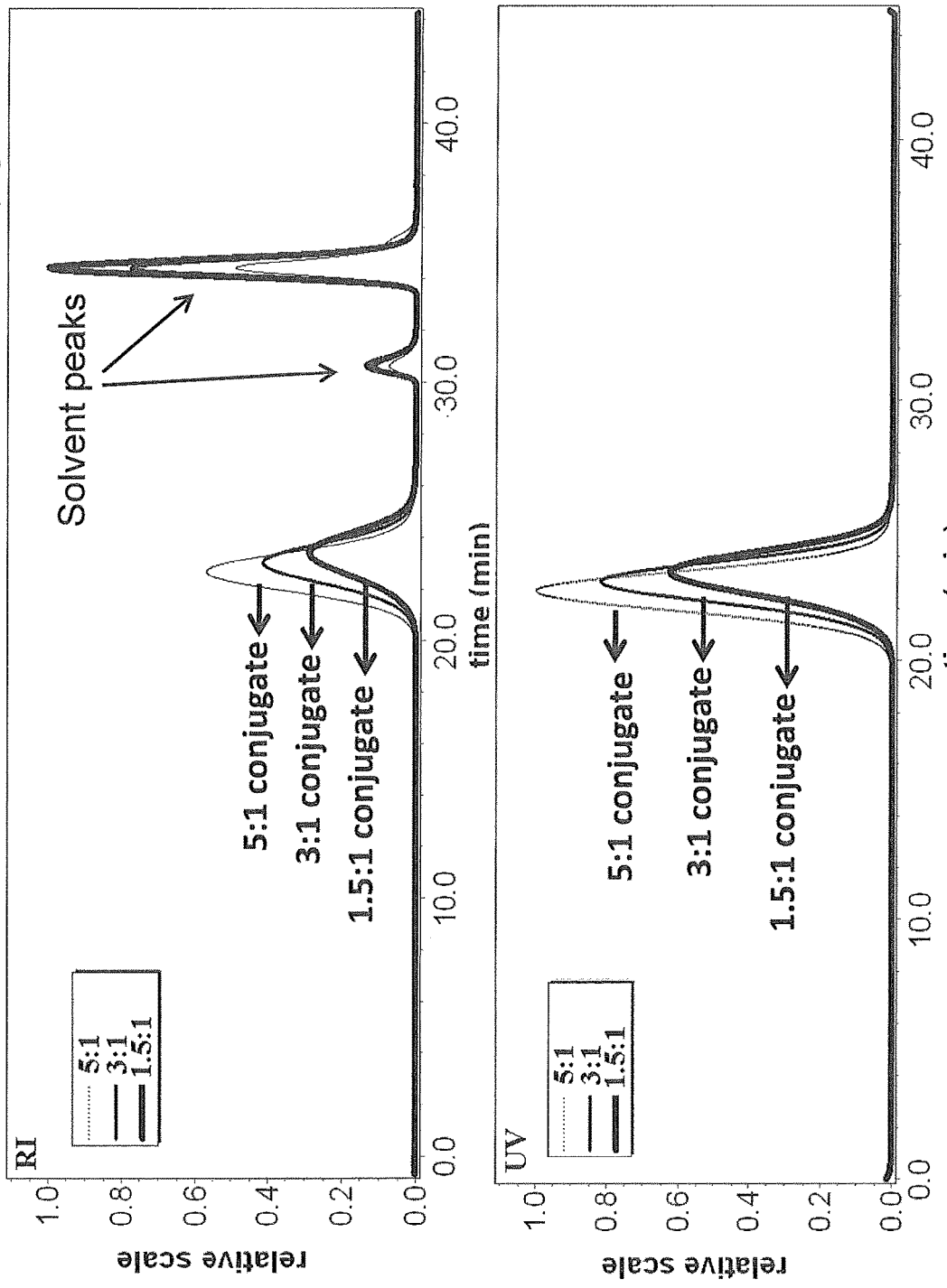
FIG. 13 confirms the purity of purified conjugate vaccine via HPLC-SEC-UV-MALLS-RI.

FIG. 13 confirms the purity of purified conjugate vaccine via HPLC-SEC-UV-MALLS-RI.

FIG. 14 shows purified PRP-LTS61K conjugates analyzed by IEF PAGE to confirm the purity of purified conjugate vaccine.

Table 2, below, is the result of a GM1 binding assay that confirms that LTS61K protein retained its binding activity following conjugation.

TABLE 2

| | 0.2/2 w PRP-LTS61K conjugate | 0.2/4 w PRP-LTS61K conjugate | 0.4/2 w PRP-LTS61K conjugate | 0.4/4 w PRP-LTS61K conjugate |
|---|---|---|---|---|
| GM1-binding activity (unit = M) | $5.19 \times 10^{-10}$ | $4.77 \times 10^{-10}$ | $4.23 \times 10^{-10}$ | $2.79 \times 10^{-10}$ |

Mammalian pre-clinical studies showing efficacy of the polysaccharide-LTS61K conjugates:

New Zealand White rabbits were immunized intramuscularly three times, at two week intervals, using the intended human dose of the polysaccharide, polysaccharide mixed with LTS61K, or polysaccharide-LTS6K conjugate to evaluate the potency of the conjugate vaccines. All vaccine preparations contained no $AlPO_4$ or other related adjuvant. The immune responses of all vaccines were determined by ELISA to detect anti-polysaccharide antigen specific IgG titers and serum bactericidal assay to detect the functional activity of the antibodies. The study results indicated that only successfully conjugated polysaccharide-LTS61K vaccines could induce higher polysaccharide-specific IgG antibody titers and greater bactericidal activity in sera than that of polysaccharide alone, or polysaccharide mixed with LTS61K only. The animal immunogenicity studies suggest that detoxified *E. coli* heat-labile enterotoxin holotoxin including LTS61K protein is useful as carrier protein of polysaccharide to significantly stimulate a specific immune response of polysaccharide antigens.

Reference is now made to additional Figures of drawings that pertain to results of initial mammalian studies.

FIG. 15 summarizes a rat immunogenicity study of Hib PRP-LTS61K conjugates of the present invention.

Figure 16:
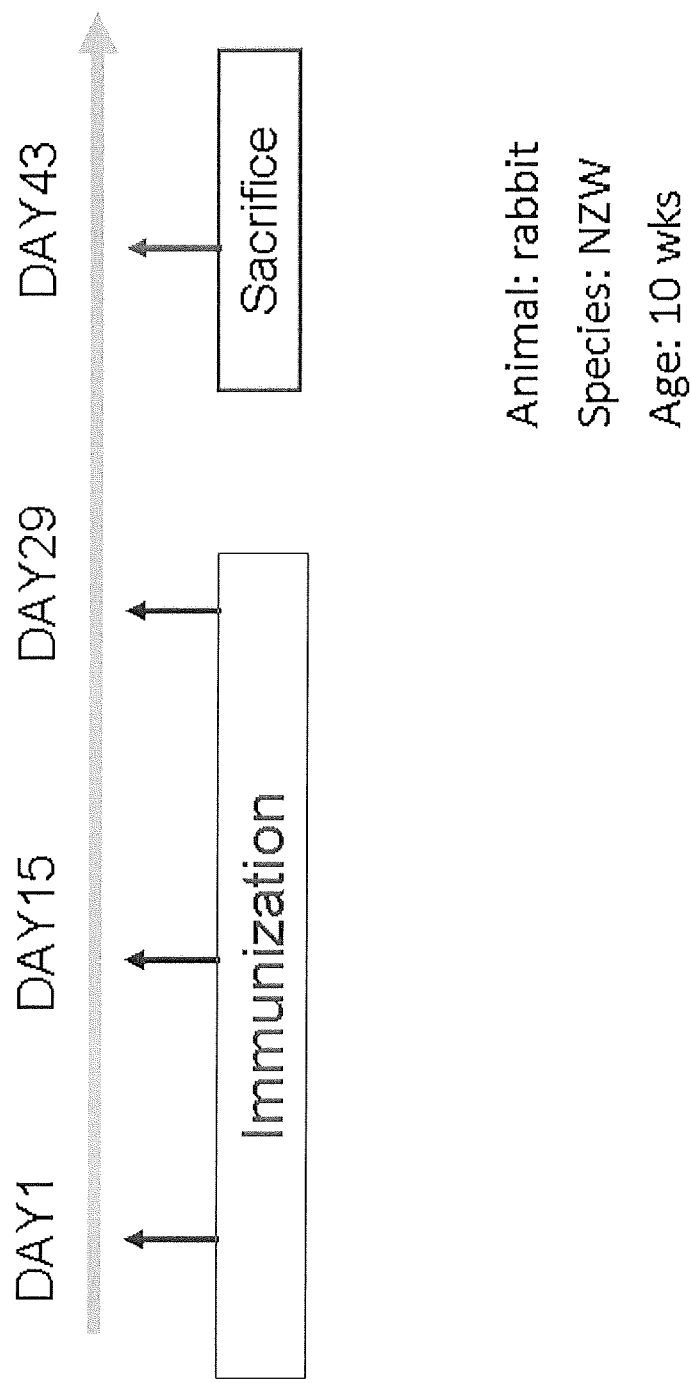
FIG. 16 summarizes a rabbit immunogenicity study of Hib PRP-LTS61K conjugates of the present invention.

FIG. 16 summarizes a rabbit immunogenicity study of Hib PRP-LTS61K conjugates of the present invention.

Figure 17:
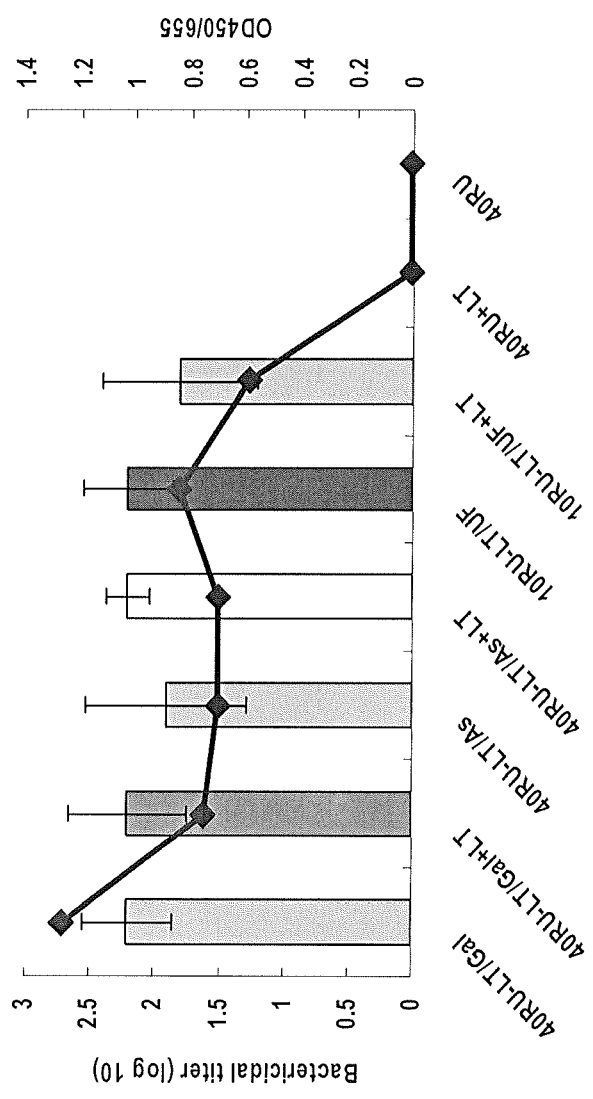
FIG. 17 illustrates results of a rabbit immunogenicity study of Hib PRP-LTS61K conjugates of the present invention, results of the rabbit serum bactericidal titer assay and anti-PRP 1gG Ab titers.

FIG. 17 illustrates results of a rabbit immunogenicity study of Hib PRP-LTS61K conjugates of the present invention, results of the rabbit serum bactericidal titer assay and anti-PRP 1gG Ab titers. Only the PRP-LTS61K conjugates were able to induce anti-PRP IgG Ab titers. The extra added LTS61K into the PRP-LTS61K conjugates did not enhance the anti-PRP IgG Abs.

Figure 18:
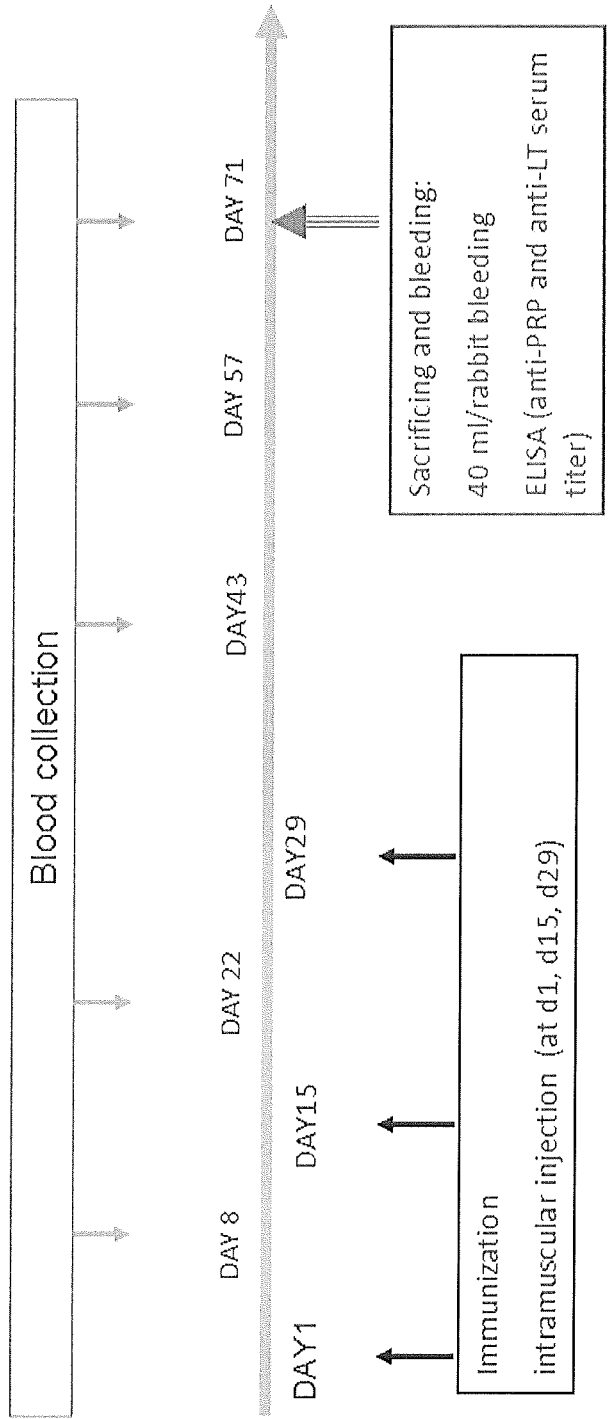
FIG. 18 illustrates additional information about the rabbit immunogenicity study.

FIG. 18 illustrates additional information about the rabbit immunogenicity study.

Figure 19:
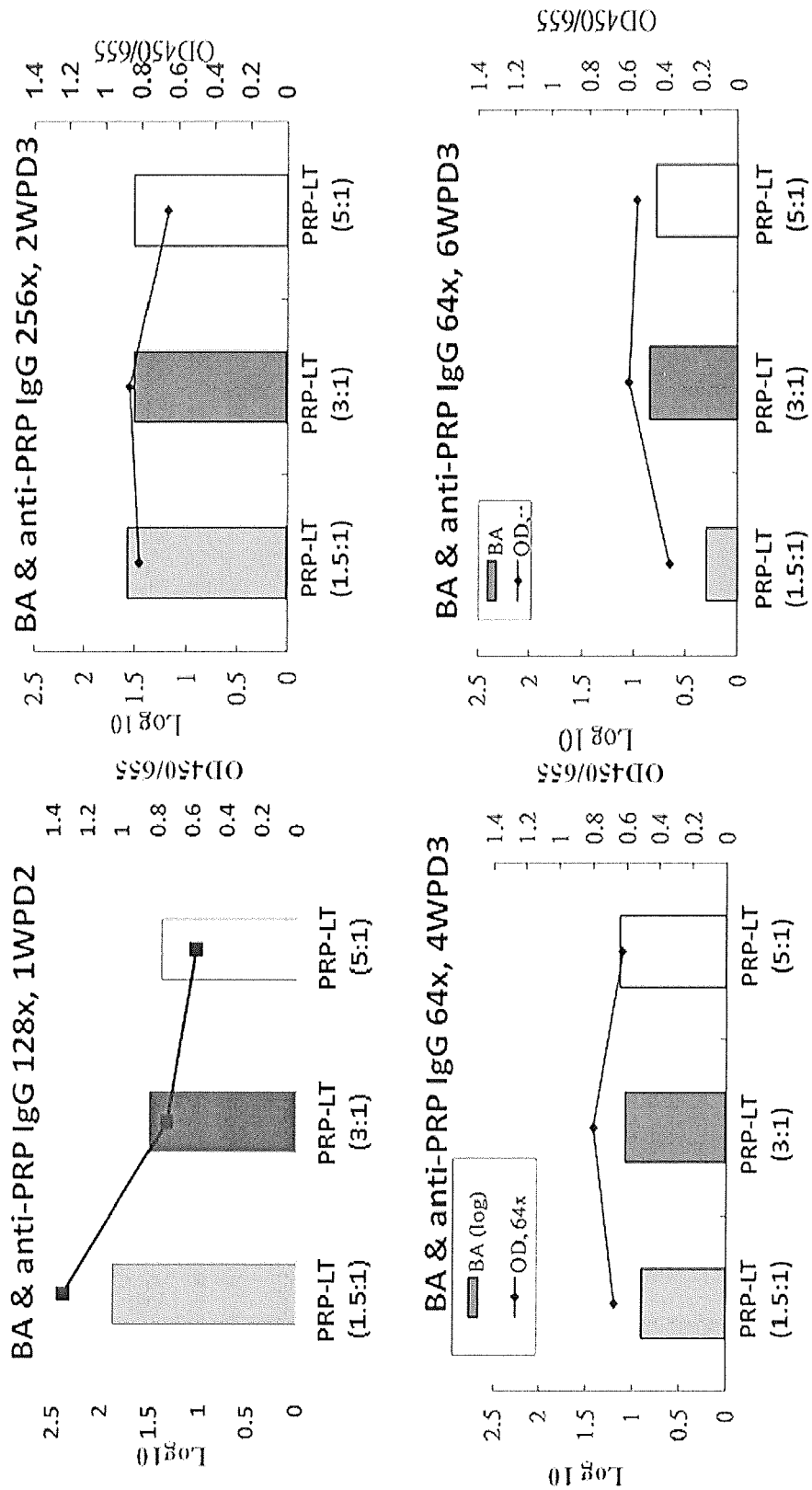
FIG. 19 illustrates results of a rabbit immunogenicity study of Hib PRP-LTS61K conjugates of the present invention, results of the rabbit serum bactericidal titers (BA) and anti-PRP IgG Ab titers (OD).

FIG. 19 illustrates results of a rabbit immunogenicity study of Hib PRP-LTS61K conjugates of the present invention, results of the rabbit serum bactericidal titers (BA) and anti-PRP 1gG Ab titers (OD).

Additional studies were conducted employing the procedures and observing the results set forth below:

New Zealand White rabbits were immunized intramuscularly three times and four times, at two week intervals, using the intended human dose of the polysaccharide, polysaccharide mixed with LTS61K, and polysaccharide-LTS61K conjugate to evaluate the potency of the conjugate vaccines. All preparations contained no $AlPO_4$ or other related adjuvant. The immune responses of all vaccines were determined by ELISA to detect anti-polysaccharide antigen specific IgG titers and serum bactericidal assay to show the functional activity of the antipolysaccharide antibodies. The responses of sera anti-LTS61K IgG titers were also determined by ELISA, and in vitro Caco-2 cell cAMP induction and Y-1 adrenal cell toxicity rounding up study were used to determine the sera anti-LTS61K Ab neutralizing ability with the wild type LT. In vivo rabbit ileal loop challenge studies were conducted to examine the function of the anti-LTS61K antibodies. The animal immunogenicity studies suggest that detoxified *E. coli* heat-labile enterotoxin holotoxin including LTS61K protein is useful as carrier protein of polysaccharide to significantly stimulate a specific response of polysaccharide antigens. LTS61K, itself, can be used as an immunogen, and, effectively produces antibodies against wild type LT.

A. Rabbit immunogenicity studies. Rabbit immunization intramuscularly using 10 ug dose of PRP, with test articles including: PRP, PRP conjugated with LTS61K and PRP mixed with LTS61K; two and three boosters were given at biweekly intervals. Blood samples were collected at 14 days after each immunization, and collected serum samples were stored at −80° C. until use.

B. Anti-polysaccharide and anti-LTS61K antibodies determined by ELISA. PRP-BSA conjugate was coated on the 96-well plate in the concentration of PRP at 100 ng/well for anti-PRP antibodies determination, and coated with LTS61K at 250 ng/well for the anti-LTS61K antibodies determination. The coated plates were incubated for 16 hours at 4° C., and following incubated with 5% skim milk as blocking buffer for one hour at 37° C. Animal sera were tested starting from a dilution of 1:50. Specific antibodies were measured using a horseradish peroxidate-conjugated goat anti-rabbit IgG incubated for 1 hour at 37° C., and revealed the antibodies by adding TMB (tetramethyl benzidine) peroxidase substrate, and after 10 minutes, the reaction was terminated by the addition of 12% $H_2SO_4$ and the absorbance was read at OD (optical density) 650-450 nm (reference wavelength 650 nm). The ELISA titers were expressed as the reciprocal of the last dilution which gave OD 450≥0.5.

C. Serum bactericidal assay. Antibody dependent complement mediated bactericidal activity was conducted for the serum diluted titers that kill more than 50% of the *Haemophilus influenzae* type b (Hib) colonies. Serum samples were pretreated in 56° C. for 30 minutes to inactivate the complement of rabbit serum. Two fold serial dilutions of the serum samples with volume of 10 uL in 96-well U-bottom plates were prepared. Following, added 20 uL of the diluted Hib culture which was prepared in 1000 CFU/20 uL. The mixtures were further incubated at 37° C. with 5% $CO_2$ for 15 minutes, and added 50 uL of the 1:1 hank's buffer diluted baby rabbit complement into each well, and incubated the mixture at 37° C. with 5% $CO_2$ for 60 minutes. Plated 5 uL of the baby rabbit complement added mixture in the chocolate agar plates, and incubated the plates at 37° C. with 5% $CO_2$ for 16 hours. Counted the Hib colony forming units and determined the serum dilution titers that killed more than 50% Hib colonies. All the serum samples are compared with the reciprocal number of dilution titers in graphics.

D. Induction of cAMP study in Caco-2 cells by the neutralized wild type LT with rabbit anti-LTS61K serum antibody was performed, using a cyclic AMP (cAMP) EIA kit (Enzo Life Science). Ten nanograms of wild type LT were incubated with 150 uL anti-LTS61K rabbit serum (1:100 dilution) at room temperature. After one hour incubation, the mixture was added to the Caco-2 cell plate ($5\times10^4$ cell/well), and Caco-2 cells were further incubated at 37° C. with 5% CO2 for 2 hours. Following, cells were washed with PBS, and lysed with 0.1M HCL (200 uL per well), and neutralized with 0.1M NaOH. The cell lysis products were collected by centrifugation at 660×G for 10 mins at room temperature. The resultant suspensions were assayed for intracellular cAMP levels by utilizing the commercial EIA kit.

E. Neutralization study of wild type LT with serious dilutions of rabbit anti-LTS61K serum was examined on Y-1 mouse adrenal tumor cells. For the Y-1 cell assay, serial two fold dilutions of rabbit sera 50×, 100× to 102,400× were premixed with wild type LT $10^{-5}$ ug (which is the EC50, that the toxin concentration of the wild type LT to produce greater than 50% cell rounding up on Y-1 adrenal cell), following the mixture were added to Y-1 adrenal cell, $5\times10^4$ cells/well. The cells were observed for morphological changes (cell rounding up) after 24 hours incubation.

F. Rabbit ileal loop fluid accumulation study: the neutralization of the rabbit anti-LTS61K serum antibody against the wild type LT was conducted in the rabbit ileal loop assay. Rabbit ileal loops with 5.5 cm segments were made on the rabbits after being immunized with PRP or PRP conjugated with LTS61K or PRP mixed with LTS61K. Wild type LT in the concentration ranges from 0.01 to 1 ug were administrated to each study animal; the amount of fluid accumulated in each segment was measured after 18 hours.

Figure 20:
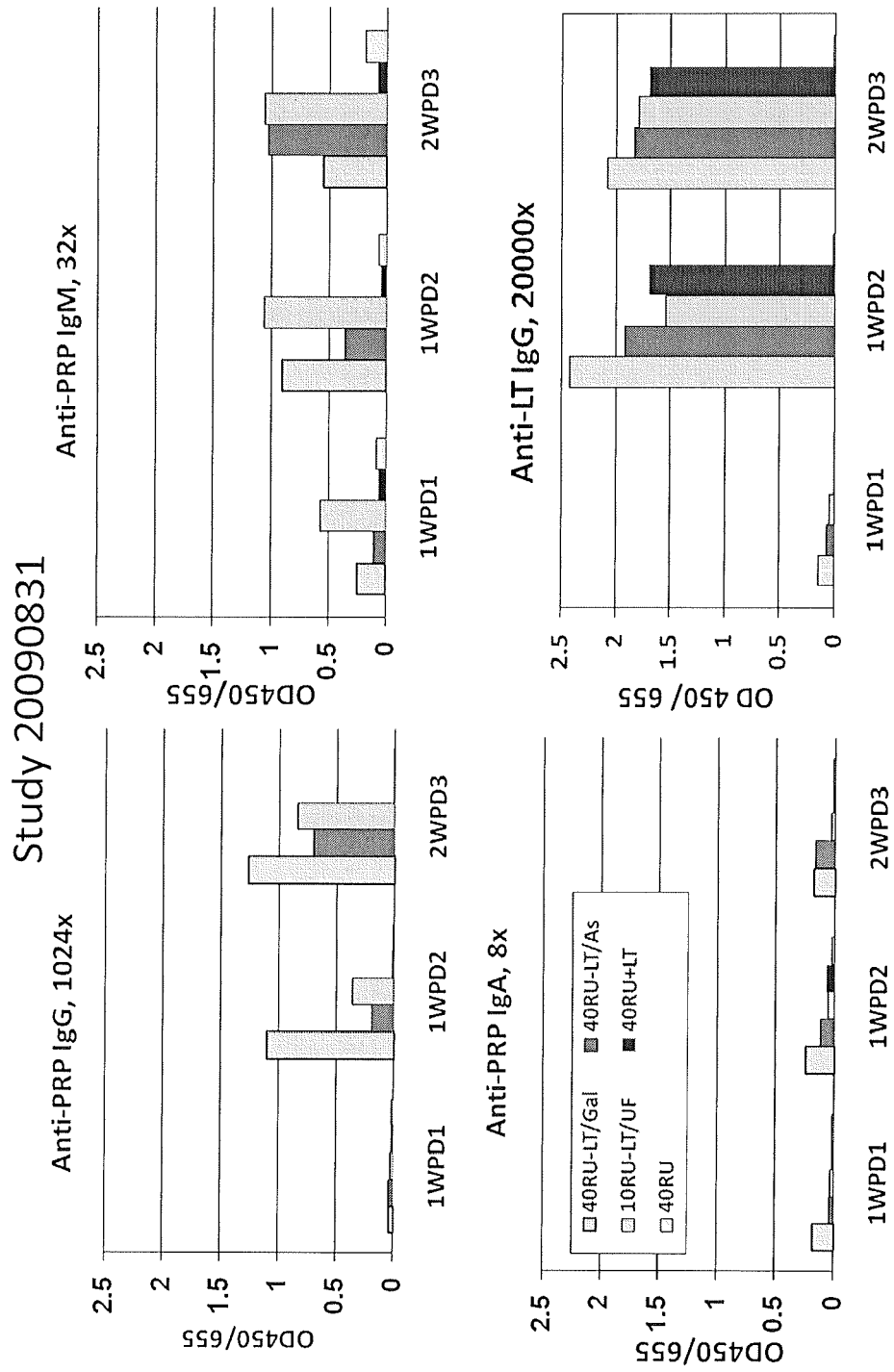
FIG. 20 shows results of additional rabbit immunogenicity ELISA of anti-PRP and anti-LTS61K antibodies response studies.

Results of the Immunogenicity Effect of Polysaccharide Conjugated with LTS61K: Mammalian Pre-Clinical Studies Showing Efficacy of the Polysaccharide-LTS61K Conjugates The study results are described below with reference to FIGS. 20 through 23 of the drawings and Tables 3 through 5.

Antibodies to PRP and to LTS61K were determined by ELISA. Results of immunogenicity in rabbits were shown in FIG. 20; only rabbits given PRP-LTS61K conjugates three injections elicit high anti-PRP IgG antibody titers and were 1000-fold greater than PRP or PRP mixed with LTS61K. The major immunoglobulin induced by PRP-LTS61K conjugates vaccine was IgG. The presence of high titer of anti-LTS61K IgG antibody did not interfere with the immune response of anti-PRP IgG Ab.

In FIG. 20, which shows the rabbit immunogenicity ELISA of anti-PRP and anti-LTS61K antibodies response results, all animals received a total of three intramuscular doses each of 10 ug conjugated PRP at 2 week intervals. Sera were collected and assayed at one week post dose 1 (1WPD1), one week post dose 2 (1WPD2) and two weeks post dose 3 (2WPD3) as depicted in FIG. 20.

The protective potential of the anti-PRP antibodies induced by the conjugates were evaluated by testing the bactericidal activity of the rabbit sera. The bactericidal titers were determined against *Haemophilus influenzae* type b (Hib) Eagen strain, data were presented as reciprocal serum dilution that killed more than 50% of the Hib colonies. FIG. 21 shows that rabbits after three times intramuscular immunization, at two week intervals, in PRP 10 ug per dose, the anti-PRP IgG Abs and bactericidal titers were similar in all of the three batches of in-house prepared PRP-LTS61K conjugates, with the conjugated PRP average repeating units in 40 or 10, and the PRP-LTS61K conjugates doses 10 ug/48 ug to 10 ug/30 ug per dose. Meanwhile, PRP and PRP mixed with LTS61K immunized rabbit sera were unable to kill the Hib bacterial, which reciprocal titers <2, and could not elicit anti-PRP IgG antibodies as well. Only the successful PRP-LTS61K conjugates have a bactericidal effect with the high titers of anti-PRP antibodies.

Figure 21:
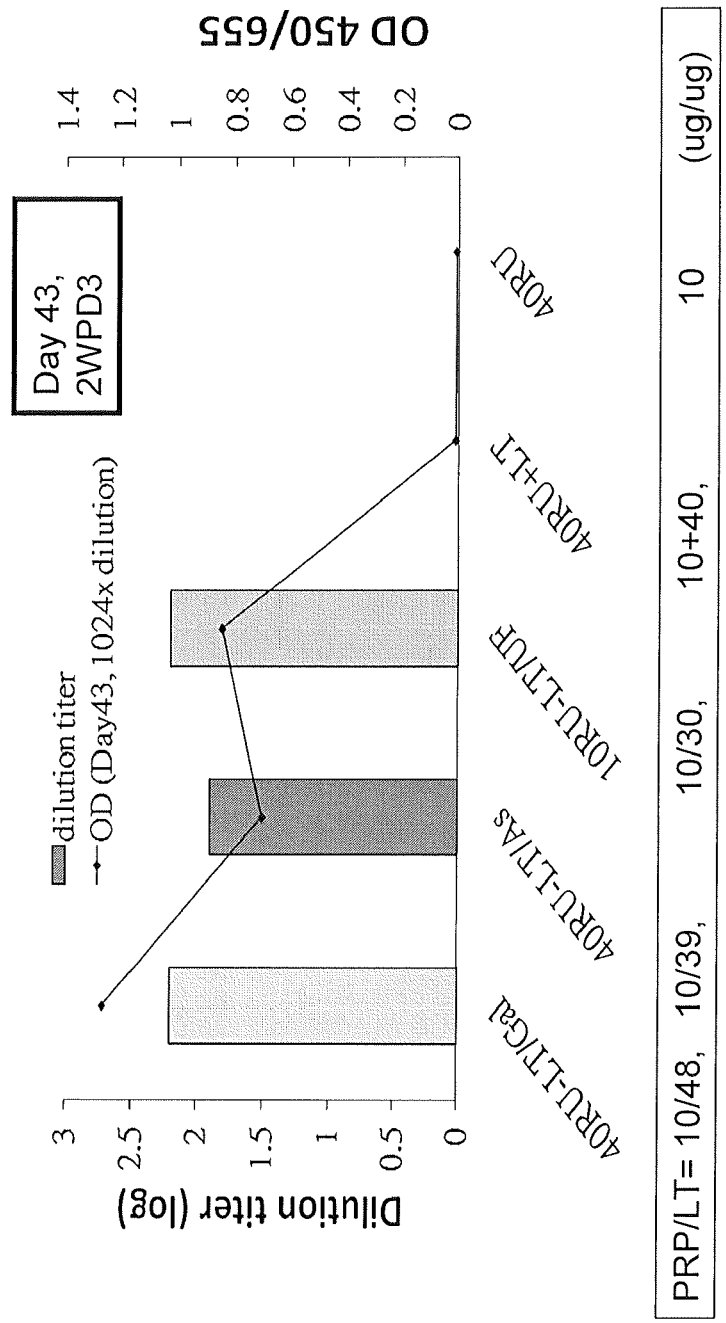
FIG. 21 shows the results of additional rabbit serum bactericidal assay and anti-PRP IgG Ab.

FIG. 21 shows rabbit serum bactericidal assay and anti-PRP IgG antibodies responses after rabbits received three intramuscular doses each of 10 ug conjugated PRP at 2 week intervals. Tested sera were collected at day 43, two weeks post dose 3.

A re-boosted study was conducted on rabbits after they received a primary-three immunization of the PRP-LTS61K conjugates. The results are summarized in FIG. 22, which demonstrated bactericidal titers and anti-PRP IgG antibodies titers gradually decreased with time, although 6WPD3 (6 weeks post dose 3) rabbit sera bactericidal titers were lower than the rabbit sera 2WPD3, the rabbit sera anti-PRP IgG antibodies and bactericidal titers could be effectively enhanced after a following dose of PRP-LTS61K conjugates. However, these phenomena could not be observed on the PRP or PRP mixed with LTS61K immunized rabbits.

Figure 22:
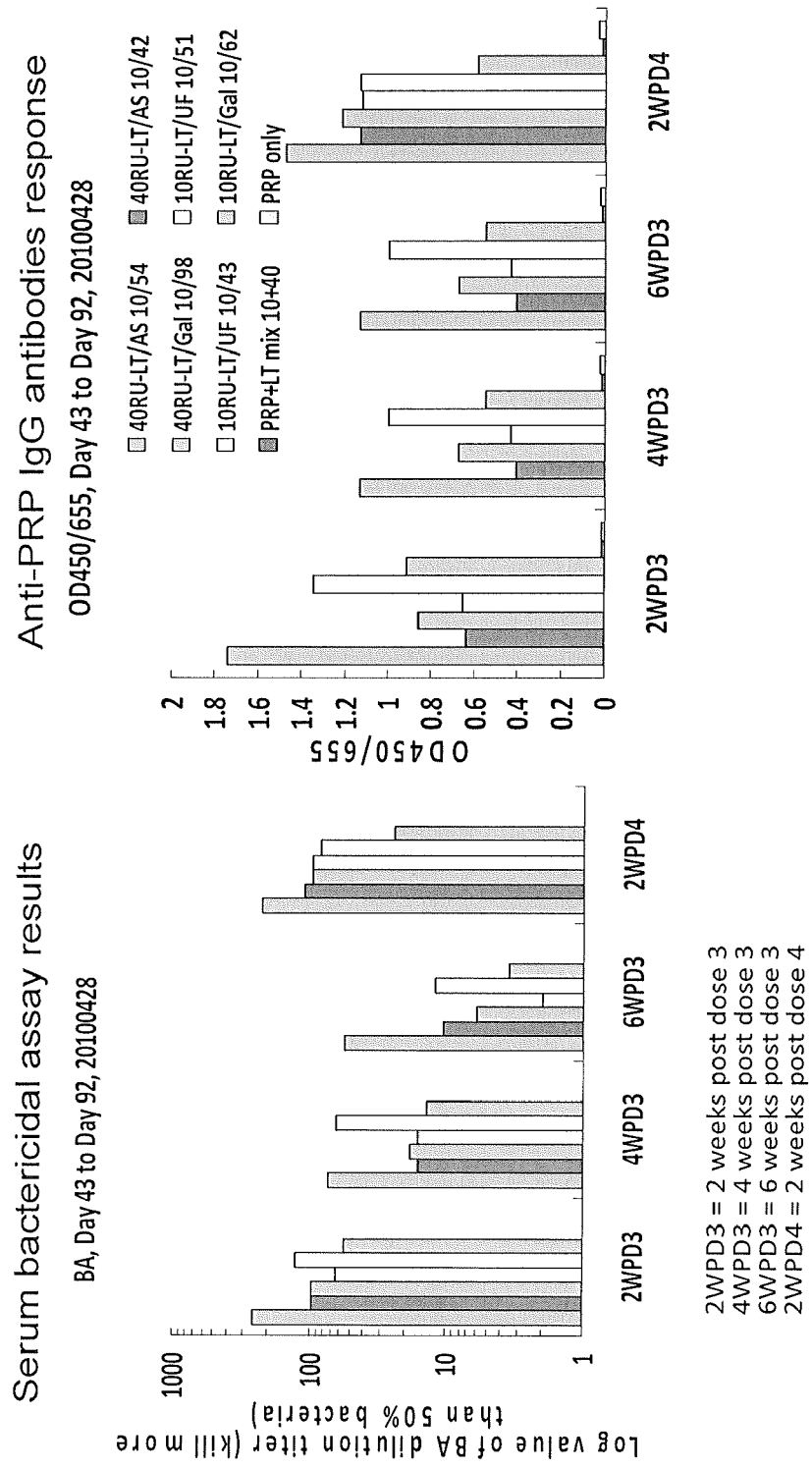
FIG. 22 shows results of additional rabbit serum bactericidal assay and anti-PRP IgG Ab after a fourth immunization.

Regarding FIG. 22, rabbits were immunized with different ratios of PRP-LTS61K conjugates. The sera were obtained at different times, and ELISA anti-PRP IgG Abs and bactericidal assays were performed. The results demonstrate correlations between the serum anti-PRP IgG antibodies and the serum bactericidal activities, and that a $4^{th}$ immunization on rabbits with PRP-LTS61K conjugates effectively re-boosts the anti-PRP Abs.

Table 3 shows that wild type LT toxin at 10 ng was unable to stimulate an increase of intracellular releasing of the cAMP levels in Caco-2 cells, only when rabbit sera with high anti-LTS61K antibodies; those were PRP-LTS61K conjugates and PRP mixed with LTS61K immunized rabbit sera. In contrast, rabbit sera obtained from PRP immunized rabbits did not prevent wild type LT from increasing cAMP levels in Caco-2 cells.

TABLE 3

Induction of cAMP study in Caco-2 cells by the neutralized wild type LT with rabbit anti-LTS61K serum antibody.

| Samples | Rabbit immunized PRP/LTS61K (ug/ug) | cAMP (pmol/mL) |
|---|---|---|
| PRP-LTS61K conjugate | 10/45 | 3.36 |
| PRP-LTS61K conjugate | 10/53 | 2.68 |
| PRP mixed with LTS61K | 10 + 45 | 3.31 |
| PRP | 10 | 19.1 |

TABLE 3-continued

Induction of cAMP study in Caco-2 cells by the neutralized wild type LT with rabbit anti-LTS61K serum antibody.

| Samples | Rabbit immunized PRP/LTS61K (ug/ug) | cAMP (pmol/mL) |
|---|---|---|
| Positive control wt LT 10 ng | — | 30.89 |
| Negative control PBS | — | 3.09 |

A neutralization study of wild type LT with serial dilutions of rabbit anti-LTS61K serum was conducted on Y-1 mouse adrenal tumor cells. The results in Table 4 demonstrate that only those rabbits' sera present with the anti-LTS61K antibodies effectively neutralize the toxicity of the wild type LT, which occurred on PRP-LT61K conjugates and PRP mixed with LTS61K immunized rabbit sera, but not in sera of rabbits immunized with PRP.

TABLE 4

Neutralization Study

| Samples | Rabbit immunized PRP/LTS61K (ug/ug) | Y-1 adrenal cell neutralization titer |
|---|---|---|
| PRP-LTS61K conjugate | 10/45 | 3200 X |
| PRP-LTS61K conjugate | 10/53 | 3200 X |
| PRP mixed with LTS61K | 10 + 45 | 3200 X |
| PRP | 10 | No neutralization |

The data in Table 5 shows that at the concentration of 0.01 ug per 5.5 cm segment ileal loop of wild type LT fluid accumulation was induced in the rabbit with no anti-LTS61K antibodies; however, in the rabbit with anti-LTS61K antibodies, there was no fluid accumulation. These results confirm those previously obtained in vitro Caco-2 cAMP induction and Y-1 adrenal cell neutralization studies, that serum anti-LTS61K antibodies are able to neutralize the wild type LT. Severe hemorrhagic lesions on ileum mucosa were observed on the rabbit without anti-LTS61K Ab administered with wild type LT in 0.5 and 1.0 ug per segment.

TABLE 5

Rabbit ileal loop fluid accumulation study.

| Wild type LT dose (ug/segment) | Rabbit without anti-LTS61K Ab | | Rabbit no.1 with anti-LTS61K Ab | | Rabbit no.2 with anti-LT Ab | |
|---|---|---|---|---|---|---|
| | Fluid accumulation (mL/segment*) | Lesions on ileum mucosa** | Fluid accumulation (mL/segment) | Lesions on ileum mucosa | Fluid accumulation (mL/segment) | Lesions on ileum mucosa |
| 0 | 0.0 | — | 0.0 | — | 0.0 | — |
| 0.01 | 4.95 | — | 0.0 | — | 0.0 | — |
| 0.1 | 8.8 | + | 0.0 | — | 4.4 | — |
| 0.5 | 10.45 | ++ | Not done | Not done | 11.0 | — |
| 1 | 12.1 | +++ | 11.0 | + | 11.0 | — |

*Fluid accumulation is measured in each 5.5 cm segment of rabbit ileal loop.
**Severe hemorrhagic lesions on ileum mucosa were observed on the rabbit without anti-LTS61K Ab administered wild type LT in 0.5 and 1.0 ug per segment.

Figure 23:
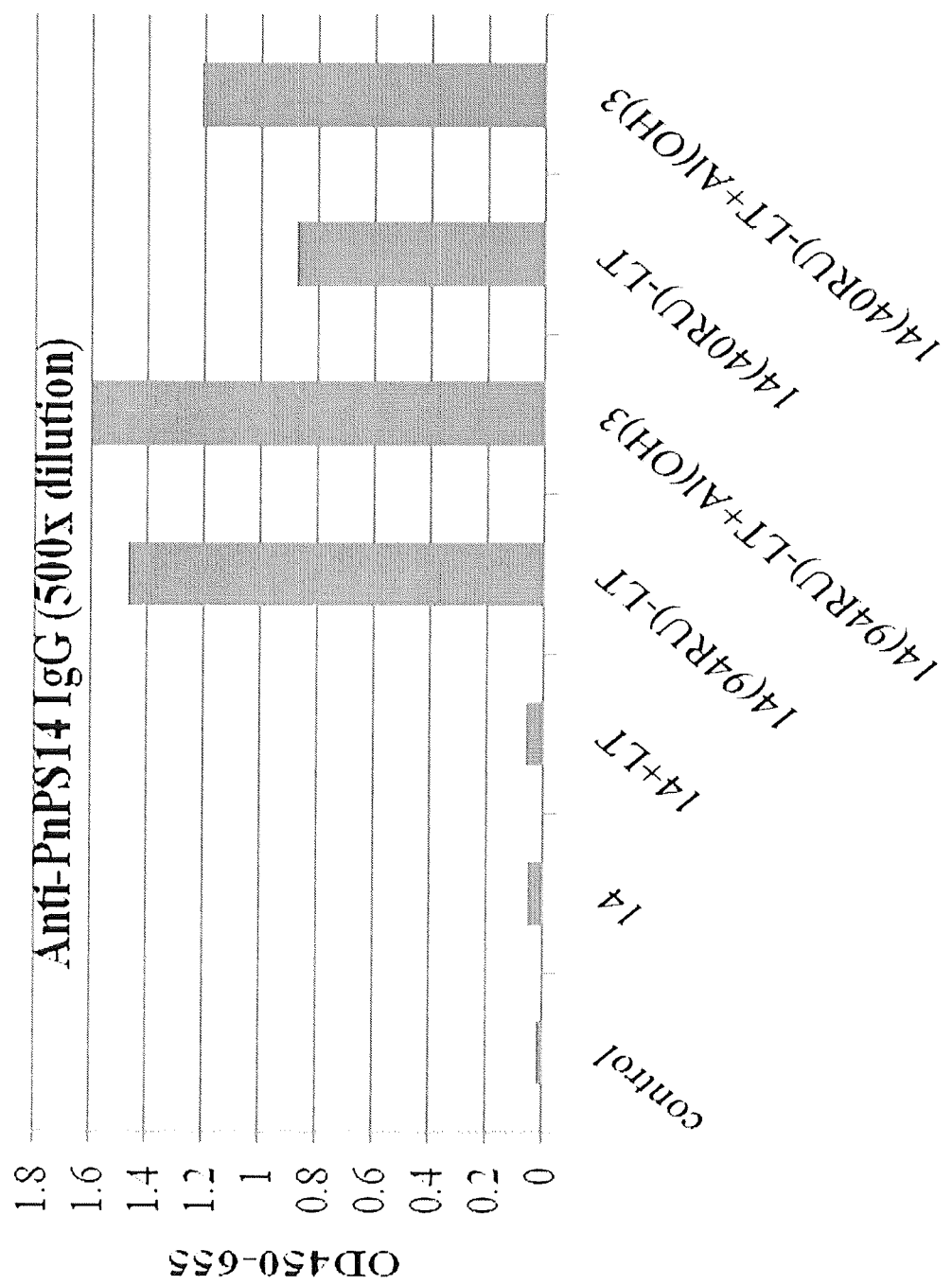
FIG. 23 shows the immunogenicity in mouse on pneumococcal PS serotype 14-LTS61K conjugates.

The results of an animal immunogenicity study as an example of pneumococcal polysaccharide serotype 14 covalent conjugated with LTS61K is shown in FIG. 23. Antibody titers to PNPS serotype 14 were determined by ELISA. Samples were PNPS14-LTS61K conjugates with PS average repeating units of 94 or 40, PNPS14 alone, PNPS14 mixed with LTS61K, and PBS. Only the conjugated products were able to induce high anti-PNPS14 IgG antibodies. The presence of the chemical adjuvant, aluminum hydroxide, during the immunization program did not benefit or significantly enhance the anti-PNPS14 antibodies.

FIG. 23 shows the immunogenicity in mice on pneumococcal PS serotype 14-LTS61K conjugates. Only animals given PNPS14-LTS61K conjugates elicit high anti-PS IgG antibody titers and were 500-fold greater than PNPS14 or PNPS14 mixed with LTS61K.

Many modifications and alterations of the present invention will become apparent to those skilled in the art without departing from the spirit and scope of the present invention which is defined by the claims.

What is claimed is:

1. A conjugate comprising a polysaccharide and a detoxified *E. coli* heat labile enterotoxin (LT), wherein the LT is a holotoxin comprising a mutant protein LT61 that exhibits GM-1 binding activity and comprises the wild type amino acid sequence of SEQ ID NO: 1 but with a lysine amino acid residue at a position corresponding to position 61 in SEQ ID NO: 1 to form the mutant protein LTS61K having reduced toxicity compared to the wild type amino acid sequence while retaining immunogenicity, the polysaccharide being configured with aldehyde end groups and being covalently conjugated to the LT holotoxin through reductive amination to form the conjugate as a soluble product in which the mutant protein LT61 retains GM-1 binding activity, wherein the polysaccharide is a bacterial capsular polysaccharide antigen from *Haemiophilus influenzae* type b or *Streptococcus pneumonia*.

2. The conjugate of claim 1 where the bacterial capsular polysaccharide is polyribosylribitol phosphate.

3. An immunogenic composition for administration to mammals which comprises the conjugate of claim 1.

4. An immunogenic composition comprising the conjugate of claim 1, wherein the immunogenic composition does not comprise an adjuvant.

5. The conjugate of claim 1, wherein the conjugate consists of the polysaccharide and the detoxified *E. coli* heat labile enterotoxin (LT).

6. The conjugate of claim 1, wherein the polysaccharide is cleaved into fragments by periodate oxidation.

7. The conjugate of claim 1 wherein the polysaccharide is a bacterial capsular polysaccharide antigen from *Streptococcus pneumonia*.

* * * * *

SEQUENCE LISTING

```
<160> NUMBER OF SEQ ID NOS: 5

<210> SEQ ID NO 1
<211> LENGTH: 240
<212> TYPE: PRT
<213> ORGANISM: Artificial Sequence
<220> FEATURE:
<223> OTHER INFORMATION: Synthetic polypeptide

<400> SEQUENCE: 1

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240

<210> SEQ ID NO 2
<211> LENGTH: 240
<212> TYPE: PRT
<213> ORGANISM: Artificial Sequence
<220> FEATURE:
<223> OTHER INFORMATION: Synthetic polypeptide
```

<400> SEQUENCE: 2

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Lys Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240

<210> SEQ ID NO 3
<211> LENGTH: 240
<212> TYPE: PRT
<213> ORGANISM: Artificial Sequence
<220> FEATURE:
<223> OTHER INFORMATION: Synthetic polypeptide

<400> SEQUENCE: 3

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Arg Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

```
Val Ser Ala Leu Gly Gly Ile Pro Tyr Ser Gln Ile Tyr Gly Trp Tyr
            115                 120                 125

Arg Val Asn Phe Gly Val Ile Asp Glu Arg Leu His Arg Asn Arg Glu
130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
            165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
            195                 200                 205

Ile Tyr Leu Arg Lys Tyr Gln Ser Lys Val Lys Arg Gln Ile Phe Ser
            210                 215                 220

Asp Tyr Gln Ser Glu Val Asp Ile Tyr Asn Arg Ile Arg Asn Glu Leu
225                 230                 235                 240
```

<210> SEQ ID NO 4
<211> LENGTH: 240
<212> TYPE: PRT
<213> ORGANISM: Artificial Sequence
<220> FEATURE:
<223> OTHER INFORMATION: Synthetic polypeptide

<400> SEQUENCE: 4

```
Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
            35                  40                  45

Gln Thr Gly Phe Val Arg Tyr Asp Asp Gly Tyr Val His Thr Ser Leu
        50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
            85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
            115                 120                 125

Arg Val Asn Phe Gly Val Ile Asp Glu Arg Leu His Arg Asn Arg Glu
130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
            165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
            195                 200                 205

Ile Tyr Leu Arg Lys Tyr Gln Ser Lys Val Lys Arg Gln Ile Phe Ser
            210                 215                 220

Asp Tyr Gln Ser Glu Val Asp Ile Tyr Asn Arg Ile Arg Asn Glu Leu
225                 230                 235                 240
```

```
<210> SEQ ID NO 5
<211> LENGTH: 240
<212> TYPE: PRT
<213> ORGANISM: Artificial Sequence
<220> FEATURE:
<223> OTHER INFORMATION: Synthetic polypeptide

<400> SEQUENCE: 5

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Tyr Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240
```